(12) United States Patent
Partanen

(10) Patent No.: US 12,340,026 B2
(45) Date of Patent: Jun. 24, 2025

(54) TECHNIQUES FOR GESTURE RECOGNITION USING WEARABLE DEVICE DATA

(71) Applicant: Oura Health Oy, Oulu (FI)

(72) Inventor: Jukka Partanen, Mäntsälä (FI)

(73) Assignee: Oura Health Oy, Oulu (FI)

( * ) Notice: Subject to any disclaimer, the term of this patent is extended or adjusted under 35 U.S.C. 154(b) by 185 days.

(21) Appl. No.: 17/946,944

(22) Filed: Sep. 16, 2022

(65) Prior Publication Data

US 2024/0094821 A1    Mar. 21, 2024

(51) Int. Cl.
| | |
|---|---|
| *G06F 3/01* | (2006.01) |
| *A61B 5/00* | (2006.01) |
| *A61B 5/0295* | (2006.01) |
| *A61B 5/11* | (2006.01) |
| *H04W 4/029* | (2018.01) |

(52) U.S. Cl.
CPC ............ *G06F 3/017* (2013.01); *A61B 5/0295* (2013.01); *A61B 5/11* (2013.01); *A61B 5/6802* (2013.01); *A61B 5/6826* (2013.01); *A61B 5/743* (2013.01); *G06F 3/014* (2013.01); *H04W 4/029* (2018.02)

(58) Field of Classification Search
CPC ......... G06F 3/017; A61B 5/0295; A61B 5/11; A61B 5/6802; A61B 5/743; A61B 5/1112; A61B 5/1118; H04W 4/029
See application file for complete search history.

(56) References Cited

U.S. PATENT DOCUMENTS

| | | | |
|---|---|---|---|
| 2014/0350349 A1* | 11/2014 | Geurts | A61B 5/1112 600/300 |
| 2017/0039480 A1* | 2/2017 | Bitran | A61B 5/01 |
| 2017/0262064 A1* | 9/2017 | Ofir | A61B 5/11 |

* cited by examiner

*Primary Examiner* — Phuong H Nguyen
(74) *Attorney, Agent, or Firm* — Holland & Hart LLP

(57) ABSTRACT

Methods, systems, and devices for gesture recognition are described. A system may identify geographical location data associated with a user throughout a time interval and may identify a set of gesture profiles corresponding to a set of gestures associated with the geographical location data of the user. The system may additionally acquire physiological data, including motion data, associated with the user from a wearable device worn by the user and may identify a set of motion segments within the time interval based on the motion data. Additionally, the system may identify a gesture the user engaged in based on matching a motion segment of the set of motion segments to a gesture profile of the set of gesture profiles and may cause a graphical user interface (GUI) of a user device running the application to display an indication of the gesture.

20 Claims, 12 Drawing Sheets

TECHNIQUES FOR GESTURE RECOGNITION USING WEARABLE DEVICE DATA

FIELD OF TECHNOLOGY

The following relates to wearable devices and data processing, including techniques for gesture recognition using wearable device data.

BACKGROUND

Some wearable devices may be configured to collect data from users. For example, a wearable device may include one or more sensors that collect motion data from a user. Some systems associated with the wearable devices may also be able to perform various actions, such as providing certain health insights to users, based on acquired motion data.

DETAILED DESCRIPTION

Figure 1:
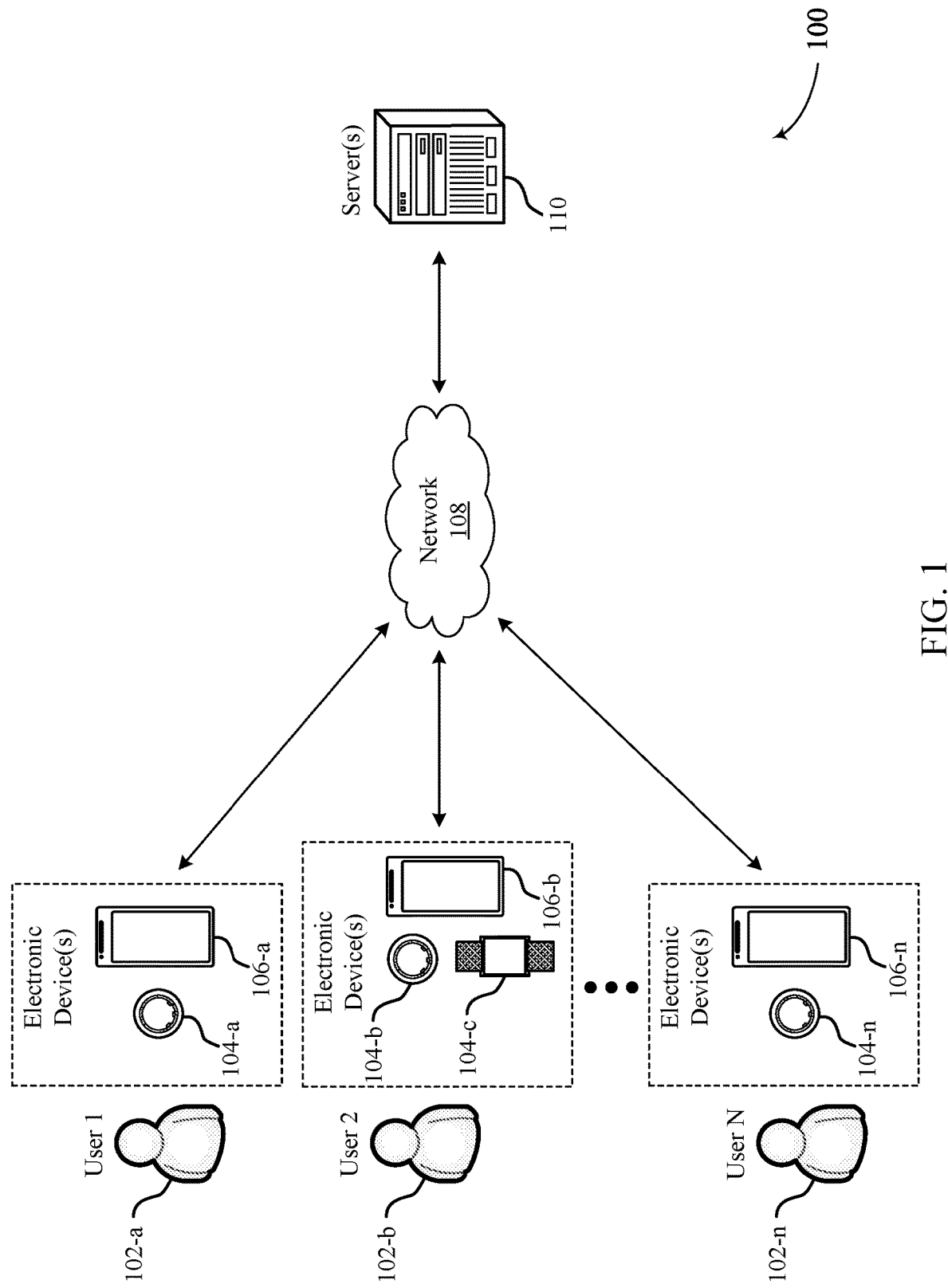
FIG. 1 illustrates an example of a system that supports techniques for gesture recognition using wearable device data in accordance with aspects of the present disclosure.

Wearable devices may be used to collect, monitor, and track physiological data associated with a user based on sensor measurements performed by the wearable device. Examples of physiological data may include temperature data, heart rate data, photoplethysmography (PPG) data, and the like. The physiological data collected, monitored, and tracked via the wearable ring device may be used to gain health insights about the user, such as the user's sleeping patterns, activity patterns, and the like. In some cases, physiological data collected by a wearable device may include motion data (e.g., acceleration data) that is used to identify certain events or movements. For example, motion data collected via a wearable device may be used to determine when the user is exercising.

Conventional wearable devices may be configured to measure an intensity (e.g., magnitude) of motion data in order to detect certain exercises. For example, an intensity of motion data may be used to differentiate between walking, running, swimming, and other types of workouts that the user may engage in. However, some wearable devices may be unable to identify specific gestures for the user, such as an eating gesture, a drinking gesture, and the like. In particular, conventional techniques that rely on an intensity/magnitude of motion data to identify different types of workouts may be unable to identify specific gestures. For instance, motion intensity may be used to determine when the user is engaged in a swimming workout, but may be unable to decipher different types of swimming strokes, or swimming "gestures."

In order to identify specific gestures, such as eating gestures, drinking gestures, sports-related gestures (e.g., swimming stroke gestures, weight-lifting gestures, racket sport gestures, golf swing gesture, etc.), or any other human activity-related gestures (e.g., driving a car, working, playing an instrument, painting, dancing, etc.), wearable devices may be configured to look for specific motion patterns or movements indicative of the respective gestures. However, there may be hundreds of different gestures that wearable devices may be looking for at any given time. As such, wearable devices may be expected to process large quantities of motion data and compare the motion data to the hundreds of potential gestures, which may result in excessive processing power and increased battery consumption. Moreover, trying to match acquired motion data to hundreds of different gestures may result in unreliable gesture detection.

Accordingly, aspects of the present disclosure are directed to techniques that leverage both physiological data collected via wearable devices and other types/sources of data, such as geographical location data and "time of day" data," to more accurately and efficiently perform gesture recognition. In particular, aspects of the present disclosure may utilize geographical location data and/or time of day data in order to narrow down a list of candidate gestures that a wearable device is expected to look for or identify. By narrowing down how many gestures that the wearable device is expected to look for at any given time, aspects of the present disclosure may reduce processing power at wearable devices associated with gesture recognition, and improve the reliability and accuracy of gesture recognition.

For example, a system may acquire geographical location data associated with a user, such as through a global positioning system (GPS), via a calendar application executable on the user device, and the like. In this example, the system may identify a set of gesture profiles associated with the geographical location of the user. For instance, if the system identifies that the user is at a restaurant, the system may identify eating-related gestures and drinking-related gestures. By way of another example, if the system identifies that the user is at a gym, the system may identify sports-related gestures (e.g., swimming stroke gestures, weight lifting gestures, running/walking stride gestures). Subsequently, the system may provide the identified gesture profiles to the wearable device, where the wearable device is configured to identify motion segments within acquired motion data, and compare the identified motion segments to the received gesture profiles. By narrowing down the list of potential gestures that the wearable device/system is looking for based on the geographical location of the user, techniques described herein may be used to improve the efficiency and reliability of gesture recognition. For instance, techniques described herein may enable the wearable device to identify quantities/repetitions of specific weight-lifting gestures (e.g., ten bicep curl gestures, followed by eight bench press gestures), quantities of running stride gestures, etc.

Other sources or types of data may also be used to improve gesture recognition, such as time of day data. For example, a user may drink coffee every morning between 7:00 am and 10:00 am, regardless of the user's actual location (e.g., at work, at home, etc.). In this example, the system may recognize that the user engages in drinking gestures during this time interval every morning, either based on previously-identified drinking gestures, user-inputted tags (e.g., the user tagging "coffee/caffeine consumption" during the mornings), or both. Accordingly, the system may identify that it is likely the user will engage in a drinking gesture in the mornings, and may therefore transmit drinking-related gesture profiles to the wearable device so that the wearable device is configured to compare received motion data to the received gesture profiles in order to identify drinking-related gestures.

In this regard, the system described herein may be configured to leverage historical gesture data associated with the user to improve gesture recognition. That is, the system associated with the wearable ring device may identify a set of gestures previously performed by the user at the location and/or during a certain time of day, such that the set of gestures indicated to the wearable ring device may include the previously performed gestures. In some implementations, identified gestures may be displayed to the user via a graphical user interface (GUI) of a user device. In some implementations, the user may be able to confirm, deny, and/or edit identified gestures to further improve gesture recognition.

Aspects of the disclosure are initially described in the context of systems supporting physiological data collection from users via wearable devices. Aspects of the disclosure are then described in the context of a gesture relationship and an example GUI. Aspects of the disclosure are further illustrated by and described with reference to apparatus diagrams, system diagrams, and flowcharts that relate to techniques for gesture recognition using wearable device data.

FIG. 1 illustrates an example of a system 100 that supports techniques for gesture recognition using wearable device data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for a wearable device 104, such as a ring 104-a, to easily and efficiently identify gestures performed by a user 102. In particular, aspects of the present disclosure are directed to narrowing down a set of candidate/potential gestures to a subset of gestures based on other types/sources of information, such as geographical location data, time of day data, and the like. In other words, aspects of the present disclosure support a method of identifying a subset of gesture profiles based on a location of the user 102-a and identifying a gesture of the user 102-a based on comparing one or more motion segments associated with motion data of the user 102-a to the subset of gesture profiles.

For example, the system 100 may collect physiological data associated with the user 102-a, including motion data collected via an accelerometer sensor of the ring 104-a. In some cases, the user 102-a may perform a gesture resulting in motion data. The ring 104-a may identify the motion data and may further identify a set of motion segments performed during a time interval based on the motion data. The set of motion segments may include motion data collected throughout a time internal associated with a location of the user 102-a.

Continuing with the same example, the user device 106-a may receive geographical location data associated with the user 102-a. For example, the user device 106-a may receive the geographical location data via a GPS associated with the system 100, via a calendar application executable on the user device 106-a, or the like thereof. As such, the user device 106-a may identify a location of the user 102-a based on the geographical location data and a time interval that the user 102-a is (or was) located at the location (e.g., the time internal associated with the location of the user 102-a discussed previously).

Additionally, the user device 106-a (or the servers 110) may identify a set of gestures that the user 102-a may perform while at the identified location. That is, the user device 106-a may identify a subset of gesture profiles associated with the location from multiple gesture profiles defined within an application associated with the system 100 (e.g., defined in a gesture library). Each gesture profile may correspond to a motion segment defining the gesture performed by the user 102-a. Additionally, the user device 106-a may transmit an indication of the identified set of gesture profiles associated with the location of the user 102-a to the ring 104-a. As such, the ring 104-a may compare a motion segment of the set of motion segments to each set of motion segments associated with respective gesture profiles of the indicated set of gesture profiles (e.g., compare the identified motion segment to each gesture profile from the indicated set of gesture profiles). Thus, the wearable ring device may identify the gesture performed by the user 102-a based on matching the identified motion segment to a gesture profile from the indicated set of gesture profiles. In some cases, the ring 104-a may transmit an indication of the identified gesture to the user device 106-a, such that the user device 106-a may display an indication of the identified gesture to the user 102-a via a GUI.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
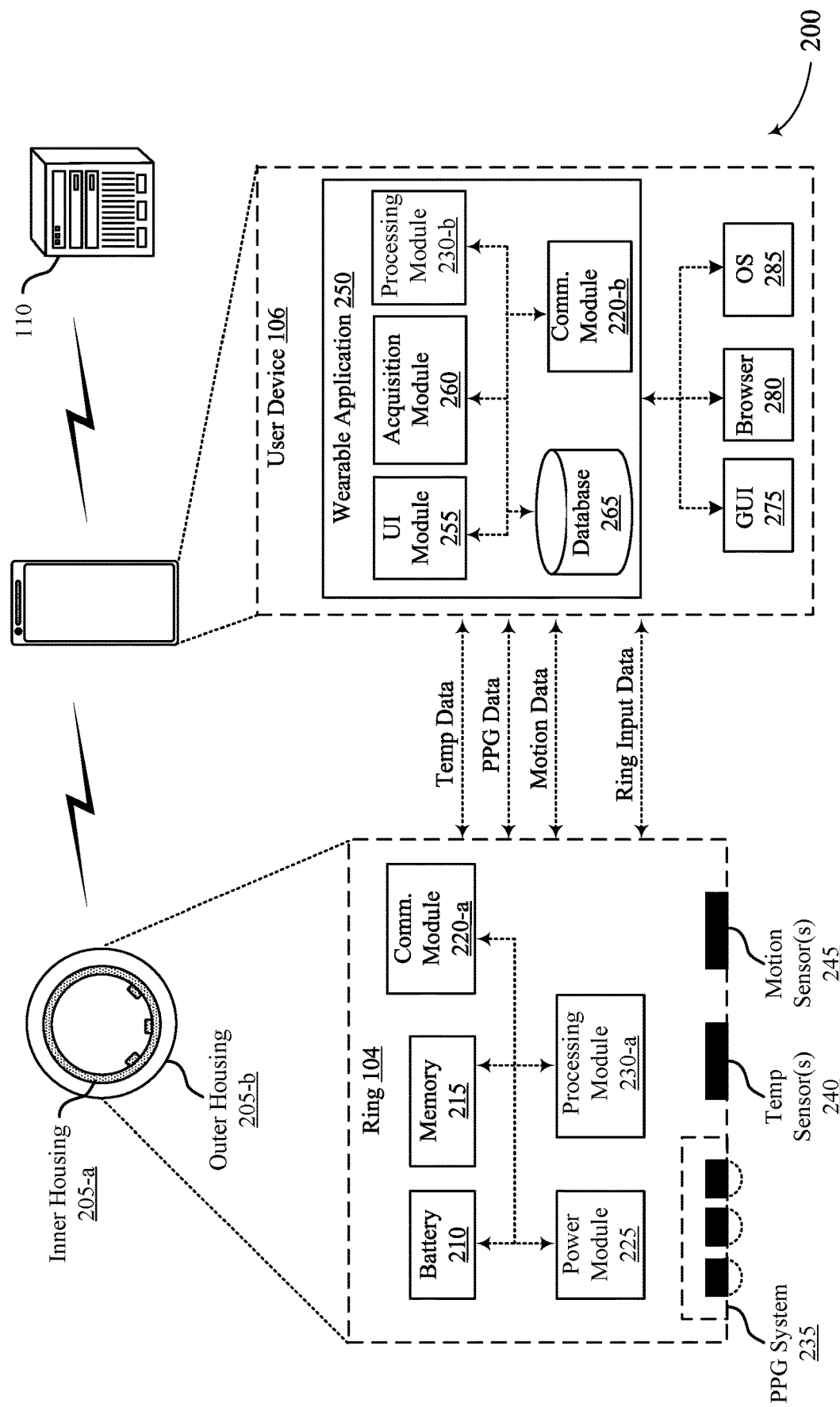
FIG. 2 illustrates an example of a system that supports techniques for gesture recognition using wearable device data in accordance with aspects of the present disclosure.

FIG. 2 illustrates an example of a system 200 that supports techniques for gesture recognition using wearable device data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for a wearable device 104, such as a ring 104, to easily and efficiently identify gestures performed by a user 102. In some aspects, techniques described herein may be used to narrow down a subset of gesture profiles that the system 200 is configured to evaluate based on other data types/sources, such as a geographical location of the user, a time of day that the user typically engages in certain gestures, and the like. In other words, aspects of the present disclosure support a method of identifying a subset of gesture profiles based on a location of the user 102 and/or a time of day that the user engages in certain gestures, and techniques for identifying a gesture of the user 102 based on comparing one or more motion segments associated with motion data of the user 102 to the subset of gesture profiles.

For example, the user device 106 of the system 200 may receive geographical location data associated with the user 102 via the acquisition module 260. For example, the user device 106 may receive the geographical location data via a GPS associated with the system 200, via a calendar application executable on the user device 106, or the like thereof. As such, the user device 106 may identify a location of the user 102 based on the geographical location data and a time interval that the user 102 is (or was) located at the location (e.g., the time internal associated with the location of the user 102 discussed previously).

Additionally, the user device 106 (or the servers 110) may identify a set of gestures that the user 102 may perform while at the identified location. That is, the user device 106 may identify a subset of gesture profiles associated with the location from multiple gesture profiles defined within the database 265 (e.g., defined in a gesture library). For example, if the user is at a restaurant, the system 200 may identify eating and drinking-related gesture profiles. Comparatively, if the user is at a gym, the system 200 may identify exercise-related gestures (e.g., weight-lifting gestures, walking/running stride gestures, etc.) Each gesture profile may correspond to a motion segment defining the gesture performed by the user 102. That is, gesture profiles may include motion segments that describe or characterize the respective gestures (e.g., gesture profiles associated with particular movements in the x, y, and z directions). For example, a "drinking gesture" may include or be defined by a period of motion in at least the y direction as the user lifts a glass or cup to their mouth, and a second period of motion as the user lowers the glass/cup back down.

The user device 106 may transmit, via the communication module 220-b, an indication of the identified set of gesture profiles associated with the location of the user 102 to the ring 104 (e.g., received via the communication module 220-a). In this example, as the ring 104 acquires motion data and identifies motion segments within the motion data, the ring 104 may compare the identified motion segments to the received gesture profiles (e.g., compare the identified motion segment to each gesture profile from the indicated set of gesture profiles). Thus, the wearable ring device may identify the gesture performed by the user 102 based on matching the identified motion segment to a gesture profile from the indicated set of gesture profiles. In some cases, the ring 104 may transmit an indication of the identified gesture to the user device 106, such that the user device 106 may display an indication of the identified gesture to the user 102 via a GUI 275.

Additionally, or alternatively, the ring 104 may acquire the motion data and forward the motion data to one or more components of the system 200, such as the user device 106 or the servers 110. Accordingly, the one or more components of the system 200 may identify the motion segments within the motion data. In some examples, the ring 104 may acquire the motion data and identify the motion segments within the motion data, forwarding the motion segments to the one or more components of the system 200. The one or more components of the system 200 may compare the motion segments (e.g., identified or received) to the identified set of gestures associated with the location of the user 102 (e.g., compare the identified motion segment to each gesture profile from the identified set of gesture profiles). Thus, the one or more components of the system 200 may identify the gesture performed by the user 102 based on matching the identified motion segment to a gesture profile from the identified set of gesture profiles. In other words, gesture recognition techniques described herein may be carried out by one or more components of the system 200, including the wearable device 104, the user device 106, the servers 110, or any combination thereof. In some cases, the one or more components of the system 200 may display an indication of the identified gesture to the user 102 via a GUI 275 (e.g., the servers 110 may transmit an indication of the identified gesture to the user device 106, such that the user device 106 may display the indication of the identified gesture).

In some implementations, the system 200 (e.g., wearable device 104, user device 106, servers 110) may be configured to utilize a classifier or other machine learning algorithm to perform gesture recognition. In particular, the system 200 may be configured to train a classifier to receive motion segments as inputs, and classify the received motion segments as corresponding to one or more potential gestures.

In some aspects, users may be able to manually define different gestures and gesture profiles. For example, in some cases, a user may initiate a "gesture definition" period via the wearable application 250, and may perform an indicated gesture during the gesture definition period such that the wearable application 250 corresponds the motion segment performed during the gesture definition period with the indicated gesture. For instance, the user may input, via the GUI 275, an indication of a drinking gesture, and may subsequently perform a drinking gesture during the gesture definition period so that the system 200 learns to associate the identified motion segment(s) with the drinking gesture (e.g., the system 200 generates a gesture profile based on motion segments identified based on the user performing the drinking gesture). In this regard, the user may manually be able to "define" or input gesture profiles that will be used for gesture recognition.

While much of the present disclosure describes the wearable device 104 as being configured to identify gestures by matching motion segments to gesture profiles, this is not to be regarded as a limitation of the present disclosure, unless noted otherwise herein. In particular, gesture identification may be performed by one or more components of system 200, including the wearable device 104, the user device 106, the servers 110, or any combination thereof.

Figure 3:
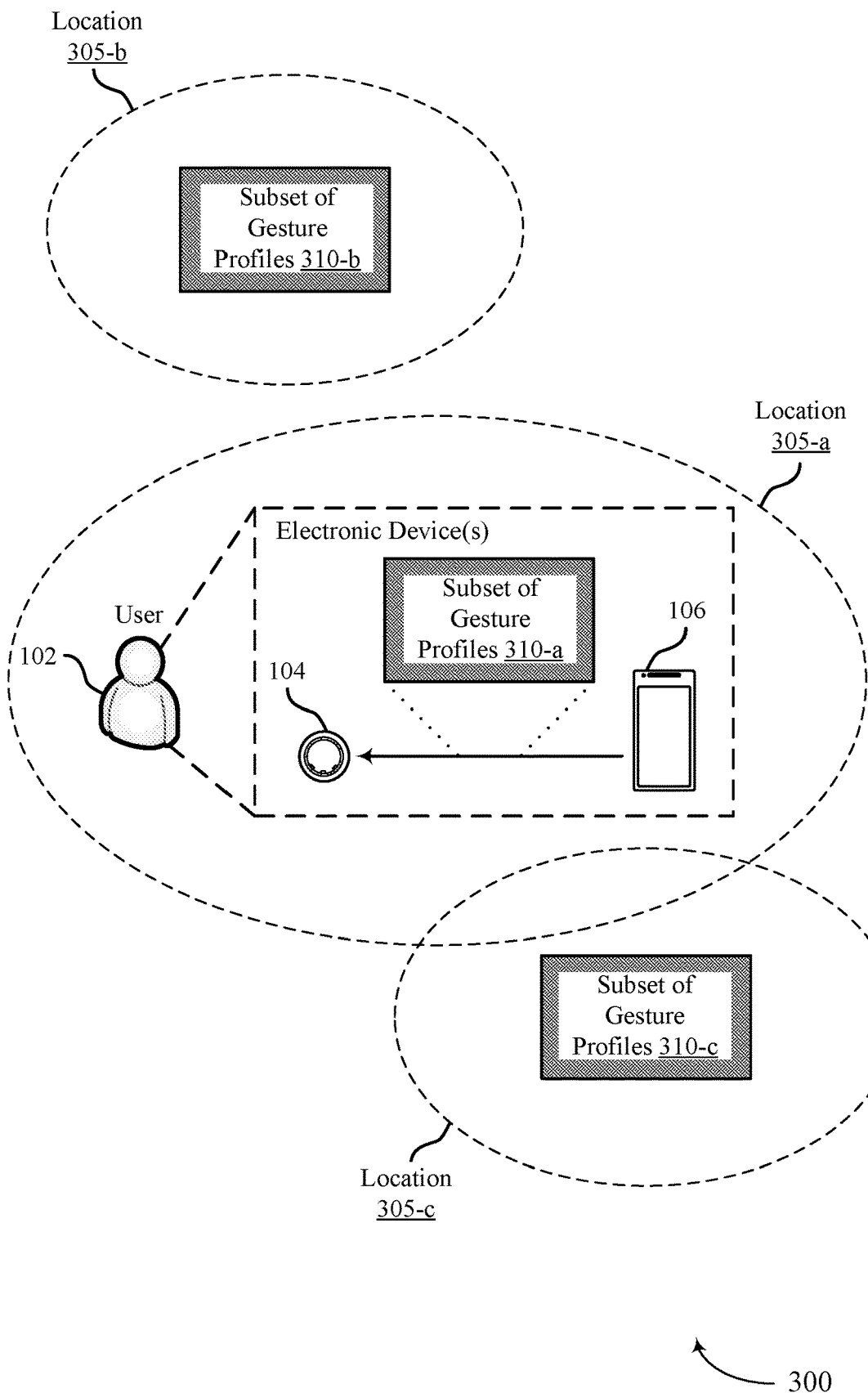
FIG. 3 illustrates an example of a system that supports techniques for gesture recognition using wearable device data in accordance with aspects of the present disclosure.

FIG. 3 illustrates an example of a system 300 that supports techniques for gesture recognition using wearable device data in accordance with aspects of the present disclosure. The system 300 may implement, or be implemented by, aspects of the system 100, the system 200, or both.

The system 300 shown in FIG. 3 illustrates an example of multiple locations 305, including a location 305-a, a location 305-b, and a location 305-c that a user 102 may be located (e.g., such as a bar, a swimming pool, a restaurant, a gym, or the like thereof). In some cases, the location 305 may be associated with a zone or other geographical boundary, as depicted by the dotted line, such that the user 102 may be considered "at the location 305" when located within the zone. Additionally, some locations 305, such as the location 305-a and the location 305-c, may overlap (e.g., the respective zones may overlap) such that the user 102 may be considered to be at both or either of the location 305-a and the location 305-c when located in the overlapping zone.

The system 200 may receive geographical location data associated with a location 305 of the user 102 throughout a time interval. That is, the system 200 may receive an indication of the location 305 (e.g., semantic location 305) that the user 102 has been located for a time threshold (e.g., the time interval). In some cases, the geographical location data may include GPS data acquired via a user device 106. Additionally, or alternatively, the system 200 may determine a location of the user (e.g., acquire geographical location data) via a calendar application executable by the user device 106, or may be obtained by any other means that the location 305 of the user 102 may be determined.

For example, a calendar application executable by the user device 106 may indicate an event (e.g., activity) that the user 102 may participate in, a location 305 of an scheduled event, or the like thereof, such that the user device 106 may determine a location 305 associated with a calendar entry. For example, as shown in FIG. 3, the calendar application may include a calendar event for "tennis" associated with a tennis center illustrated by location 305-a such that the system 200 is able to determine that the user is likely located at (e.g., within) the location 305-a for the duration of the "tennis" calendar event. Additionally, information from calendar events may enable the system 200 to "learn" or identify certain locations 305. For example, in cases where the calendar application executable by the user device 106 includes a calendar event associated with personal training at the given time, the system 200 may be configured to label or identify a location that the user is located during the personal training event as a gym.

Additionally, the system 200 (e.g., user device 106) may identify a subset of gesture profiles 310 associated with the location 305. That is, a database of the system 200 (e.g., an application associated with the ring 104) may include a set of gestures, each associated with a gesture profile, and multiple subsets of gesture profiles 310 corresponding to the respective locations 305. For example, the first location 305-a may be associated with a first subset of gesture profiles 310-a, the second location 305-b may be associated with a second subset of gesture profiles 310-b, and the third location 305-c may be associated with a third subset of gesture profiles 310-c. For instance, in cases where the first location 305-a includes a gym, the first subset of gesture profiles 310-a may include gesture profiles for exercise-related gestures, such as weight-lifting gestures (e.g., bicep curl repetition gesture, bench press repetition gesture, etc.), swimming stroke gestures, walking stride gestures, running stride gestures, and the like. Comparatively, in cases where the second location 305-b includes a restaurant or bar, the second subset of gesture profiles 310-b may include gesture profiles for eating and drinking-related gestures.

In some examples, relationships between locations 305 and corresponding subsets of gesture profiles 310 may be based on historical gesture data associated with the user 102. For example, the system 200 may identify that, during a previous time interval, the user 102 performed a first gesture while located at the location 305-a. As such, the first subset of gesture profiles 310-a may include the first gesture. In some examples, the system 200 may add a gesture profile to a subset of gesture profiles 310 associated with a location 305 based on a quantity of instances/occurrences of the gesture being performed by the user 102 at the location 305 exceeding a threshold quantity of instances (e.g., the gesture is often performed at the location 305). Alternatively, the system 200 may remove a gesture profile from a subset of gesture profiles 310 associated with a location 305 based on the user 102 not performing the gesture at the location over a period of time that exceeds a time threshold. For example, the system 200 may remove a gesture profile from a subset of gesture profiles 310 associated with a location 305 based on the user having not performed the gesture at the location 305 in over a year.

Additionally, or alternatively, relationships between locations 305 and subsets of gesture profiles 310 may be based on user input. For example, the user 102 may input, via a GUI, a user input indicating a location 305 and one or more gestures associated with the location 305. For instance, the location 305-*b* may include a tennis center where the user 102 plays tennis. As such, the user 102 may input, via the GUI, a user input indicating racket sport related gestures (e.g., tennis gestures) associated with the location 305-*b*, where gesture profiles corresponding to the inputted gestures are included within the second subset of gesture profiles 310-*b* based on the user input. In other words, the user may instruct the system 200 to look for and identify racket sport related gestures when the user is located at location 305-*b*.

Additionally, or alternatively, relationships between locations 305 and subsets of gesture profiles 310 may be based on a type of location 305. For example, a location 305 classified as a restaurant may be associated with a subset of gesture profiles 310 including the eating and drinking related gestures. By way of another example, the second location 305-*b* may include a gym, such that the subset of gesture profiles 310-*b* includes gesture profiles for weight-lifting gestures, running gestures, walking gestures, and the like.

In some implementations, the user device 106 may transmit an indication of a subset of gesture profiles 310 to the ring 104 based on the user 102 being located at the corresponding location 305. For example, if the system 200 identifies that the user is located at the first location 305-*a*, the user device 106 may transmit an indication of the first subset of gesture profiles 310 to the ring so that the ring 104 can monitor for gestures that match the first subset of gesture profiles 310-*a*.

For example, the ring 104 may receive the first subset of gesture profiles 310-*a*, and may collect physiological data, specifically motion data, associated with the user 102. In this example, the ring 104 may identify multiple motion segments within the time interval that the user 102 is (or was) at the location 305-*a* based on the motion data. In some cases, one or more of the multiple motion segments may be based on motion data associated with the user 102 performing a gesture. As such, the ring 104 may identify a gesture the user 102 engaged in (e.g., performed) based on matching a motion segment of the multiple motion segments to a gesture profile included within the first subset of gesture profiles 310-*a*.

Additionally, or alternatively, the ring 104 may collect the physiological data, specifically the motion data, associated with the user 102 and forward (e.g., transmit) the motion data to one or more components of the system 200, such as the user device 106 or the servers 110. Accordingly, the one or more components of the system 200 may identify the multiple motion segments within the time interval that the user 102 is (or was) at the location 305-*a* based on the motion data. As such, the one or more components of the system 200 may identify the gesture the user 102 engaged in (e.g., performed) based on matching the motion segment of the multiple motion segments to the gesture profile included within the first subset of gesture profiles 310-*a*.

In some examples, upon identifying that the user performed a gesture, the ring 104 may transmit an indication of the identified gesture to the user device 106, such that the user device 104 may display an indication of the identified gesture via a GUI of the user device 106, as described with reference to FIG. 5. The GUI may prompt the user 102 to confirm/deny the identified gesture, modify the identified gesture, or both.

While much of the present disclosure is described in the context of the subsets of gesture profiles 310 being associated with locations 305, this is not to be regarded as a limitation of the present disclosure. Indeed, it is contemplated herein that individual gesture profiles and/or subsets of gesture profiles 310 may be associated with one or more locations 305. In this regard, a time of day may be considered with reference to the techniques described herein. That is, subsets of gesture profiles 310 may be associated with one or more times of day, one or more locations, or both.

Figure 4:
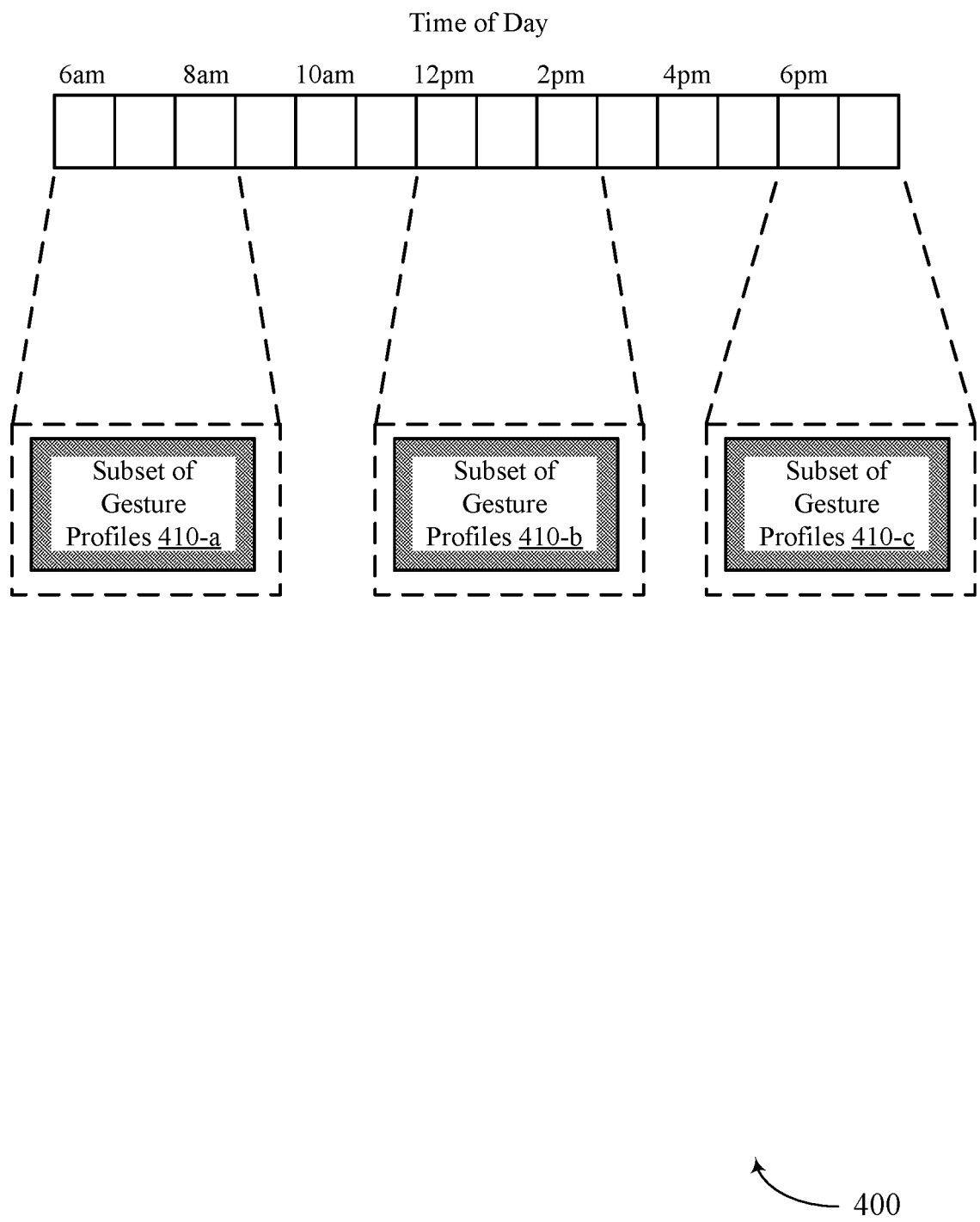
FIG. 4 illustrates an example of a gesture relationship that supports techniques for gesture recognition using wearable device data in accordance with aspects of the present disclosure.

FIG. 4 illustrates an example of a gesture relationship 400 that supports techniques for gesture recognition using wearable device data in accordance with aspects of the present disclosure. The gesture relationship 400 may implement, or be implemented by, aspects of the system 100, the system 200, the system 300, or any combination thereof.

Continuing with the example above, in some implementations, different subsets of gesture profiles 410 may additionally or alternatively be associated with different time durations (e.g., different times of day). For example, as shown in FIG. 4, a first time interval between 6 am and 9 am may be associated with a first subset of gesture profiles 410-*a*, a second time interval between 12 pm and 3 pm may be associated with a second subset of gesture profiles 410-*b*, and a third time interval between 6 pm and 8 pm may be associated with a third subset of gesture profiles 410-*c*.

As an illustrative example, the first subset of gesture profiles 410-*a* may include gesture profiles corresponding to gestures that a user typically performs early in the morning, such as a drinking gesture (e.g., drinking coffee), an eating gesture, a reading gesture, and/or other such gestures that a user 102 may perform during a morning routine. Comparatively, in cases where a user typically works out over their lunch hour, the second subset of gesture profiles 410-*b* may include gesture profiles for exercise-related gestures.

In this regard, the system 200 may be configured to provide the respective subsets of gesture profiles 410 to the wearable device 104 during the corresponding time intervals (e.g., during the corresponding times of day that the user is predicted/expected to engage in the respective gestures). For example, the user device 106 may transmit an indication of the first subset of gesture profiles 410-*a* to the wearable device 104 at or before 6 am so that the ring is configured to identify gestures corresponding to gesture profiles included within the first subset of gesture profiles 410-*a* during the time period between 6 am and 8 am.

Additionally, or alternatively, the system 200 may store an indication of the subset of gesture profiles 410, such that one or more components of the system 200, such as a user device 106 or servers 110, may identify gestures corresponding to gesture profiles included within the subset of gesture profiles 410 based on motion data received from the wearable device 104.

In some cases, each subset of gesture profiles 410 associated with a time of day may be based on historical data associated with the user 102. For example, the system 200 may identify that the user 102 typically exercises between 12 pm and 2 pm (e.g., while on a lunch break). As such, the second subset of gesture profiles 410-b may include one or more sports-related gestures, such as a running gesture, a walking gesture, a weight-lifting gesture, or the like thereof. Further, the user device 106 may transmit an indication of the second subset of gesture profiles 410-b to the ring 104 based on the time of day being between 12 pm and 2 pm.

In some implementations, the user device 106 may indicate corresponding times of day that the respective subsets of gesture profiles 410 are expected to apply. In other words, the user device 106 may transmit the second subset of gesture profiles 410-b to the wearable device 104, and may instruct the wearable device 104 to compare motion segments identified between 12 pm and 2 pm to the second subset of gesture profiles 410-b.

In some cases, the subsets of gesture profiles 410 may be based on the time of day and the location of the user 102. For example, the system 200 may identify that the user 102 typically eats dinner between 6 pm and 8pm while located at home. As such, the third subset of gesture profiles 410-c may include an eating gesture, a drinking gesture, or the like thereof. Further, the user device 106 may transmit an indication of the third subset of gesture profiles 410-c to the ring 104 based on the user 102 being located at home between 6 pm and 8 pm.

While much of the present disclosure is described in the context of eating gestures, drinking gestures, and sports-related gestures, this is not to be regarded as a limitation of the present disclosure. Indeed, it is contemplated herein that individual gesture profiles and/or subsets of gesture profiles 410 may be associated with eating, drinking, or playing a sport. In this regard, any motion (e.g., activity, gesture, etc.) performed by the user 102 may be associated with a gesture profile and may be considered with reference to the techniques described herein. That is, gesture profiles may include any human activity-related gesture (e.g., driving a car, working, playing an instrument, painting, dancing, etc.).

Figure 5:
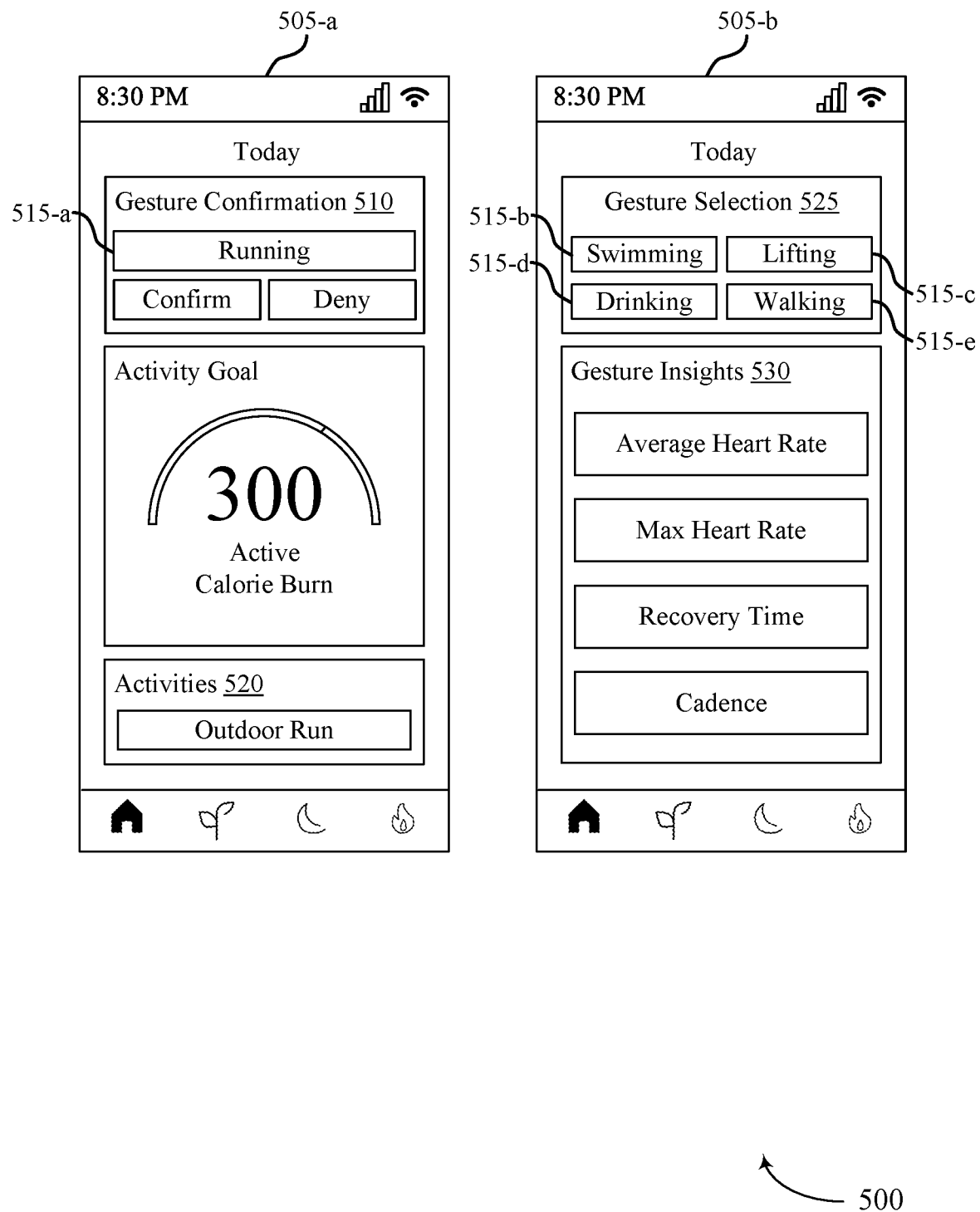
FIG. 5 illustrates an example of a graphical user interface (GUI) that supports techniques for gesture recognition using wearable device data in accordance with aspects of the present disclosure.

FIG. 5 illustrates an example of a GUI 500 that supports techniques for gesture recognition using wearable device data in accordance with aspects of the present disclosure. The GUI 500 may implement, or be implemented by, aspects of the system 100, the system 200, the system 300, the gesture relationship 400, or any combination thereof. For example, the GUI 500 may include an example of the GUI included within a user device 106.

The GUI 500 illustrates a series of application pages 505 that may be displayed to the user via the GUI 500 (e.g., GUI 275 illustrated in FIG. 2). Continuing with the example above, the ring 104 may identify a gesture 515 that the user 102 engaged in based on matching a motion segment to a gesture profile. In this example, the gesture 515 may include a gesture 515-a associated with a running gesture (e.g., running stride gesture). Upon identifying the gesture 515-a, the user 102 may be presented with the application page 505-a. As shown in FIG. 5, the application page 505-a may display an indication that the gesture 515-a was detected based on an associated motion segment. In some cases, the indication may include a gesture confirmation 510 that may prompt the user to confirm or dismiss the gesture 515-a (e.g., confirm/deny whether the ring 104 correctly detected the motion segment associated with the gesture 515-a or confirm/deny that the gesture 515-a was the gesture 515 that the user 102 performed). Additionally, or alternatively, the gesture confirmation 510 may display a confirmation message to the user indicating that the gesture 515-a was successfully recorded (e.g., automatically record the gesture 515-a without user confirmation).

In some aspects, a user input received via the gesture confirmation 510 may be used to further train a classifier or other algorithm that is configured to perform gesture recognition. In particular, a user input that confirms or denies an identified gesture may be inputted back into the classifier to further train the classifier for performing gesture recognition.

In some implementations, the gesture 515-a may be recorded/logged in a database. For example, the gesture 515-a may be logged in an activity log for the user for the respective day. In some aspects, the system 200 may associate the gesture 515-a with physiological data collected from the user 102 (e.g., during the time interval that the gesture 515-a was recorded or during a different time interval) in order to identify trends or relationships between gestures 515 and the user's physiological data (e.g., determine that running at 7 pm leads to poor quality sleep for the user). For example, if the system 200 identifies that the user was at a bar between 10 pm and midnight, and subsequently identifies that the user suffered from poor sleep, the system 200 may determine that the user likely engaged in drinking-related gestures, and may generate an insight that the user consuming alcohol late at night leads to poor quality sleep.

Moreover, in some cases, the gesture 515-a may be used to update (e.g., modify) one or more scores associated with the user (e.g., Sleep Score, Readiness Score). That is, data associated with the gesture 515-a may be used to update the scores for the user for the respective day that gesture 515-a was detected. In some cases, the application page 505-a may display the one or more scores for the user for the respective day.

In some implementations, the system 200 may identify, based on the gesture 515-a, an activity 520 (e.g., activity segment) that the user 102 is (or was) engaged, a taggable event (e.g., from a library of defined taggable events), or both. For example, the system 200 may identify that the gesture 515-a is associated with an outdoor run and may indicate the activity 520 to the user 102 via the application page 505-a. Additionally, the system 200 may identify the activity 520, the taggable event, or both, based on the geographical location data, time of day, or both. For example, the system 200 may identify a gesture 515-d associated with drinking at 6 am and may tag caffeine consumption.

In some implementations, the system 200 may be configured to log, record, or otherwise recognize data associated with a gesture 515-a without explicit confirmation from a user 102. For example, in some cases, the system 200 may identify the gesture 515-a with a sufficient degree of precision, accuracy, or reliability. In such cases, the system 200 may log or otherwise record the gesture 515-a without displaying a prompt (e.g., the gesture confirmation 510) to a user 102 and/or receiving an explicit confirmation from the user 120.

In cases where the user 102 dismisses (e.g., denies) the gesture confirmation 510 (e.g., prompt) on the application page 505-a, the gesture confirmation 510 may disappear, and the data associated with the (incorrectly) gesture confirmation 510 may not be used to update the user's 102 scores or logged in an activity log for the user 102 for the respective day. Additionally, or alternatively, the user 102 may be presented with the application page 505-b. As shown in FIG. 5, the application page 505-b may display a gesture selection 525 prompting the user 102 to select a gesture 515 that the user 102 performed during the time interval. That is, the system 200 may prompt the user 102 to edit (e.g., correct) the gesture 515 indicated via the gesture confirmation 510.

For example, the user 102 may deny the gesture confirmation 510 associated with the gesture 515-*a* and may prompt the user 102 to select a gesture 515-*b*, 515-*c*, 515-*d*, or 515-*e*. In some cases, the gestures 515-*b*, 515-*c*, 515-*d*, and 515-*e* may each be associated with additional gesture profiles from the set of gesture profiles indicated to the ring 104. Additionally, or alternatively, the gestures 515-*b*, 515-*c*, 515-*d*, and 515-*e* may each be associated with a respective motion segment that is similar to a motion segment associated with the gesture 515-*a* (e.g., may be associated with a similar gesture profile as a gesture profile associated with the gesture 515-*a*).

Conversely, in cases where the system 200 correctly identified the gesture 515-*a* (e.g., upon confirming the gesture confirmation 510 on the application page 505-*a*), the application page 505-*b* may display gesture insights 530. As shown in FIG. 5, the application page 505-*b* may display the gesture insights 530 associated with running, as identified based on the gesture 515-*a*. That is, the system 200 may collect additional physiological data (e.g., collected prior to, during, or following identification of the gesture 515-*a*) associated with the user 102 based on the gesture 515-*a* and may display the gesture insights 530 based on the additional physiological data.

As shown in FIG. 5, the gesture insights 530 may include an average heart rate of the user 102 while performing the gesture 515-*a*, a maximum heart rate of the user 102 while performing the gesture 515-*a*, a recovery time associated with performing the gesture 515-*a*, and a cadence of the user 102 while performing the gesture 515-*a*. By way of another example, the system may display gesture insights 530 indicating whether gesture 515-*a* positively or negatively impacted one or more of the users scores. For example, the application page 505-*b* may display, via the gesture insights 530, an indication that the user 102 ran within an hour of sleeping and the ring 104 recorded an increase in sleep disruption during the associated sleep period, resulting in a decrease in the user's 102 Sleep Score (e.g., the timing of running negatively affected the user's 102 Sleep Score).

Figure 6:
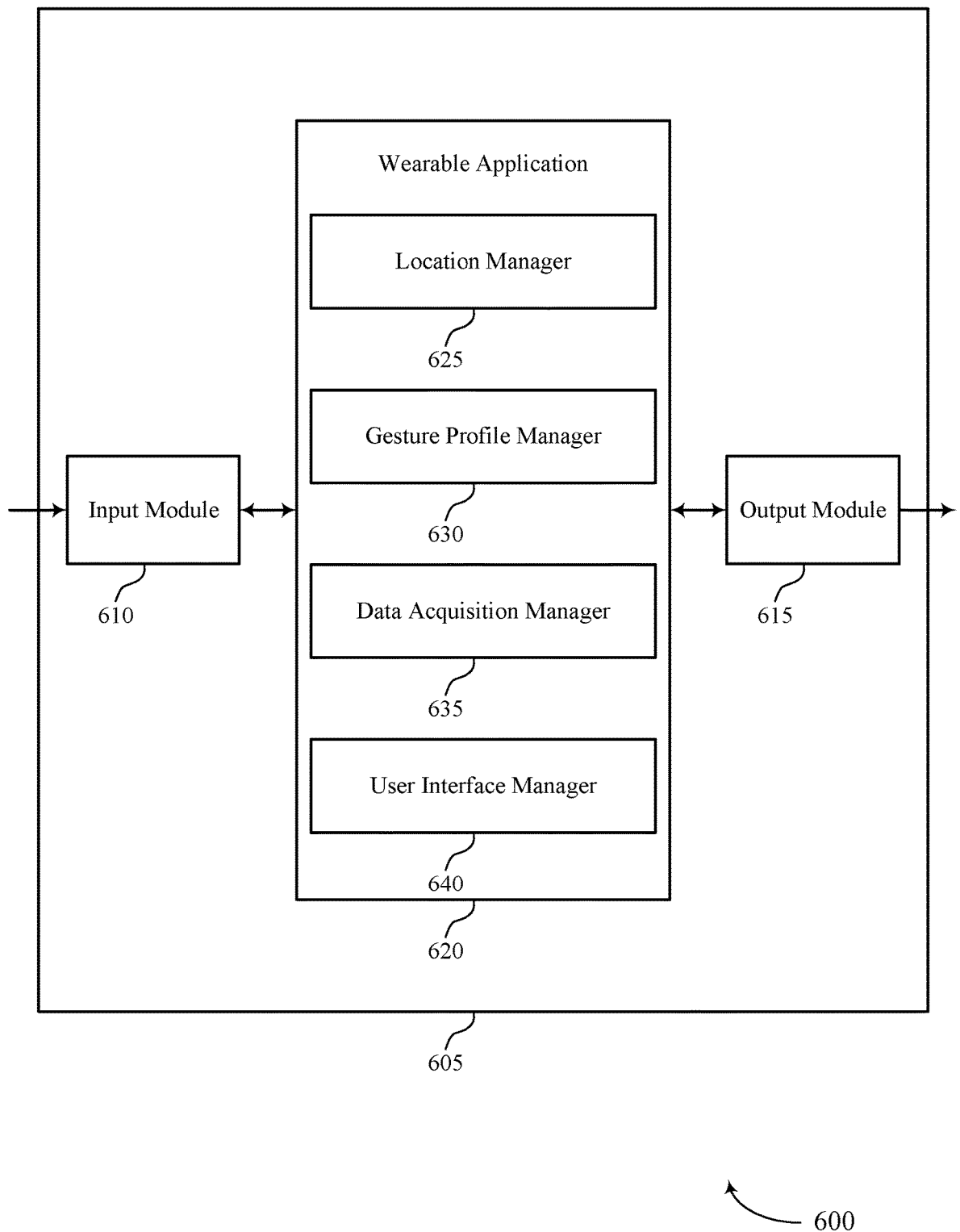
FIG. 6 shows a block diagram of an apparatus that supports techniques for gesture recognition using wearable device data in accordance with aspects of the present disclosure.

FIG. 6 shows a block diagram 600 of a device 605 that supports techniques for gesture recognition using wearable device data in accordance with aspects of the present disclosure. The device 605 may include an input module 610, an output module 615, and a wearable application 620. The device 605 may also include a processor. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include a location manager 625, a gesture profile manager 630, a data acquisition manager 635, a user interface manager 640, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The location manager 625 may be configured as or otherwise support a means for receiving geographical location data associated with a user throughout a time interval. The gesture profile manager 630 may be configured as or otherwise support a means for identifying a set of gesture profiles corresponding to a set of gestures associated with the geographical location data of the user, wherein the set of gestures are included within a plurality of gestures defined within an application associated with a wearable device. The data acquisition manager 635 may be configured as or otherwise support a means for acquiring physiological data associated with the user from the wearable device, the physiological data comprising at least motion data. The data acquisition manager 635 may be configured as or otherwise support a means for identifying a plurality of motion segments within the time interval based at least in part on the motion data. The gesture profile manager 630 may be configured as or otherwise support a means for identifying a gesture the user engaged in based at least in part on matching a motion segment of the plurality of motion segments to a gesture profile of the set of gesture profiles. The user interface manager 640 may be configured as or otherwise support a means for causing a GUI of a user device running the application to display an indication of the gesture.

Figure 7:
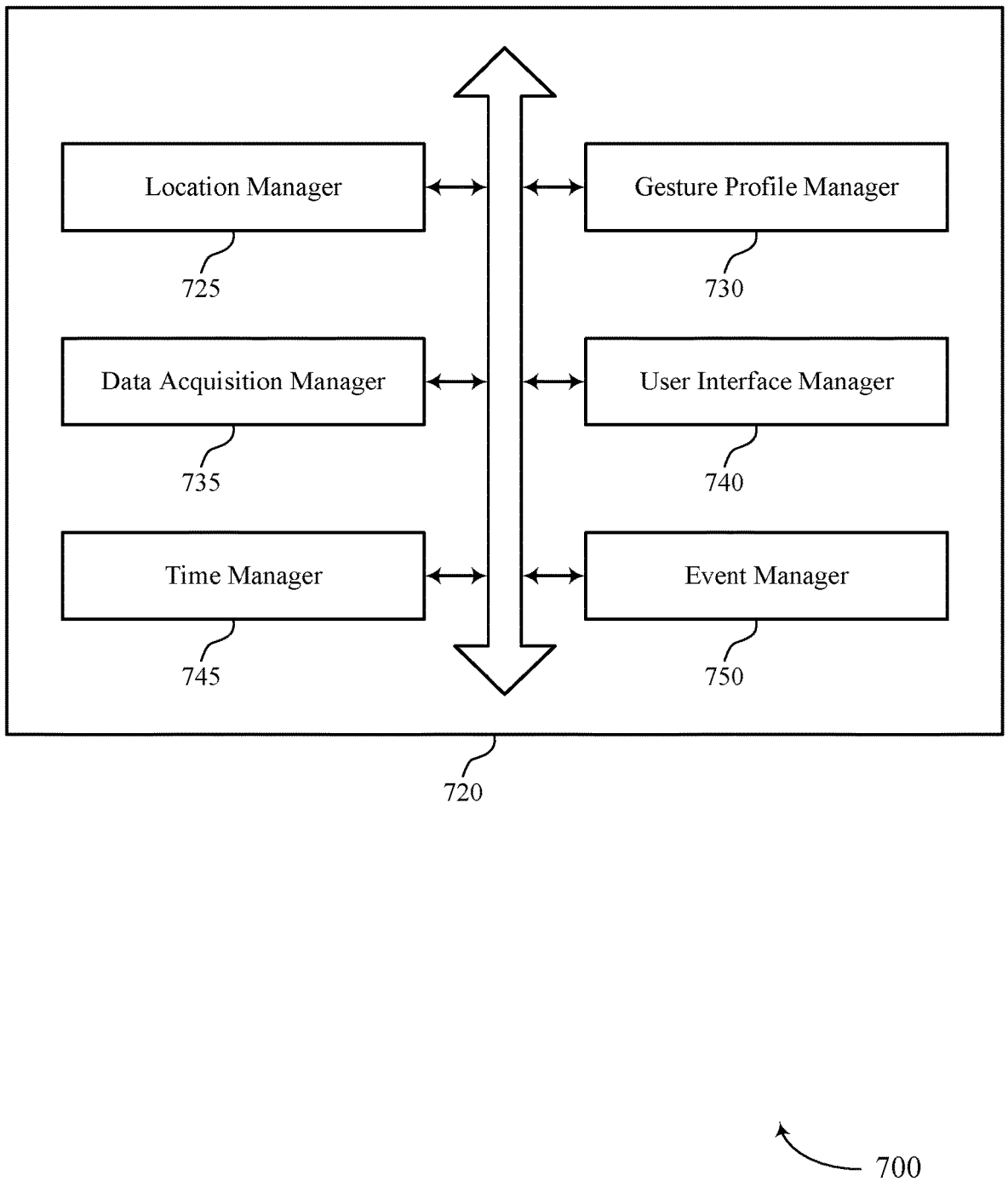
FIG. 7 shows a block diagram of a wearable application that supports techniques for gesture recognition using wearable device data in accordance with aspects of the present disclosure.

FIG. 7 shows a block diagram 700 of a wearable application 720 that supports techniques for gesture recognition using wearable device data in accordance with aspects of the present disclosure. The wearable application 720 may be an example of aspects of a wearable application or a wearable application 620, or both, as described herein. The wearable application 720, or various components thereof, may be an example of means for performing various aspects of techniques for gesture recognition using wearable device data as described herein. For example, the wearable application 720 may include a location manager 725, a gesture profile manager 730, a data acquisition manager 735, a user interface manager 740, a time manager 745, an event manager 750, or any combination thereof. Each of these components may communicate, directly or indirectly, with one another (e.g., via one or more buses).

The location manager 725 may be configured as or otherwise support a means for receiving geographical location data associated with a user throughout a time interval. The gesture profile manager 730 may be configured as or otherwise support a means for identifying a set of gesture profiles corresponding to a set of gestures associated with the geographical location data of the user, wherein the set of gestures are included within a plurality of gestures defined within an application associated with a wearable device. The data acquisition manager 735 may be configured as or otherwise support a means for acquiring physiological data associated with the user from the wearable device, the physiological data comprising at least motion data. In some examples, the data acquisition manager 735 may be configured as or otherwise support a means for identifying a plurality of motion segments within the time interval based at least in part on the motion data. In some examples, the gesture profile manager 730 may be configured as or otherwise support a means for identifying a gesture the user engaged in based at least in part on matching a motion segment of the plurality of motion segments to a gesture profile of the set of gesture profiles. The user interface manager 740 may be configured as or otherwise support a means for causing a GUI of a user device running the application to display an indication of the gesture.

In some examples, the gesture profile manager 730 may be configured as or otherwise support a means for transmitting the set of gesture profiles to the wearable device, wherein the wearable device is configured to identify the gesture by matching the motion segment to the gesture profile from the set of gesture profiles. In some examples, the gesture profile manager 730 may be configured as or otherwise support a means for receiving a message indicating the gesture from the wearable device, wherein causing the GUI to display the indication of the gesture is based at least in part on receiving the message.

In some examples, the gesture profile manager 730 may be configured as or otherwise support a means for identifying historical gesture data associated with the user, the historical gesture data comprising a plurality of historical gestures engaged in by the user and historical geographical location data corresponding to the plurality of historical gestures, wherein the plurality of historical gestures are associated with the set of gesture profiles. In some examples, the location manager 725 may be configured as or otherwise support a means for identifying that the geographical location data of the user is associated with the historical geographical location data, wherein identifying the set of gesture profiles is based at least in part on identifying that the geographical location data of the user is associated with the historical geographical location data.

In some examples, the gesture profile manager 730 may be configured as or otherwise support a means for identifying historical gesture data associated with the user, the historical gesture data comprising a plurality of historical gestures and a time of day that the user engaged in the plurality of historical gestures, wherein the plurality of historical gestures are associated with the set of gesture profiles. In some examples, the time manager 745 may be configured as or otherwise support a means for identifying that the time interval including the plurality of motion segments is within the time of day, wherein identifying the set of gesture profiles is based at least in part on identifying that the time interval is within the time of day.

In some examples, the gesture profile manager 730 may be configured as or otherwise support a means for receiving, via the GUI and based at least in part on displaying the indication of the gesture, a confirmation of the gesture, a modification of the gesture, or both.

In some examples, the event manager 750 may be configured as or otherwise support a means for identifying, based at least in part on the identified gesture, an activity segment that the user is (or was) engaged in, a taggable event included within a plurality of taggable events defined in the application, or both. In some examples, the user interface manager 740 may be configured as or otherwise support a means for causing the GUI of the user device to display an indication of the activity segment, an indication of the taggable event, or both.

In some examples, the gesture profile manager 730 may be configured as or otherwise support a means for receiving, via the GUI, a user input indicating a semantic location and the set of gestures associated with the semantic location. In some examples, the location manager 725 may be configured as or otherwise support a means for identifying that the geographical location data is associated with the semantic location, wherein identifying the set of gesture profiles is based at least in part on identifying the geographical location data is associated with the semantic location.

In some examples, the data acquisition manager 735 may be configured as or otherwise support a means for receiving additional physiological data associated with the user from the wearable device, the additional physiological data comprising additional motion data including an additional motion segment. In some examples, the user interface manager 740 may be configured as or otherwise support a means for receiving, via the GUI, a user input indicating that the additional motion segment is associated with the gesture. In some examples, the gesture profile manager 730 may be configured as or otherwise support a means for generating the gesture profile associated with the gesture based at least in part on the user input, wherein identifying the gesture is based at least in part on generating the gesture profile.

In some examples, the gesture profile manager 730 may be configured as or otherwise support a means for identifying a relationship between the identified gesture and the physiological data acquired during the time interval, additional physiological data acquired during a different time interval, or both. In some examples, the user interface manager 740 may be configured as or otherwise support a means for causing the GUI of the user device to display a message associated with the relationship.

In some examples, the event manager 750 may be configured as or otherwise support a means for selectively adjusting a Readiness Score associated with the user, an Activity Score associated with the user, or both, based at least in part on the identified gesture. In some examples, the geographical location data comprises geographical positioning data acquired via the user device. In some examples, the geographical location data is received via a calendar application executable by the user device.

In some examples, the set of gestures comprise an eating gesture, a drinking gesture, a sports-related gesture, or any combination thereof. In some examples, the sports-related gesture comprises a swimming stroke gesture, a racket sport gesture, a walking or running stride gesture, a golf swing gesture, a weight-lifting gesture, or the like thereof. In some examples, the wearable device comprises a wearable ring device. In some examples, the wearable device collects the physiological data from the user based on arterial blood flow, capillary blood flow, arteriole blood flow, or a combination thereof.

Figure 8:
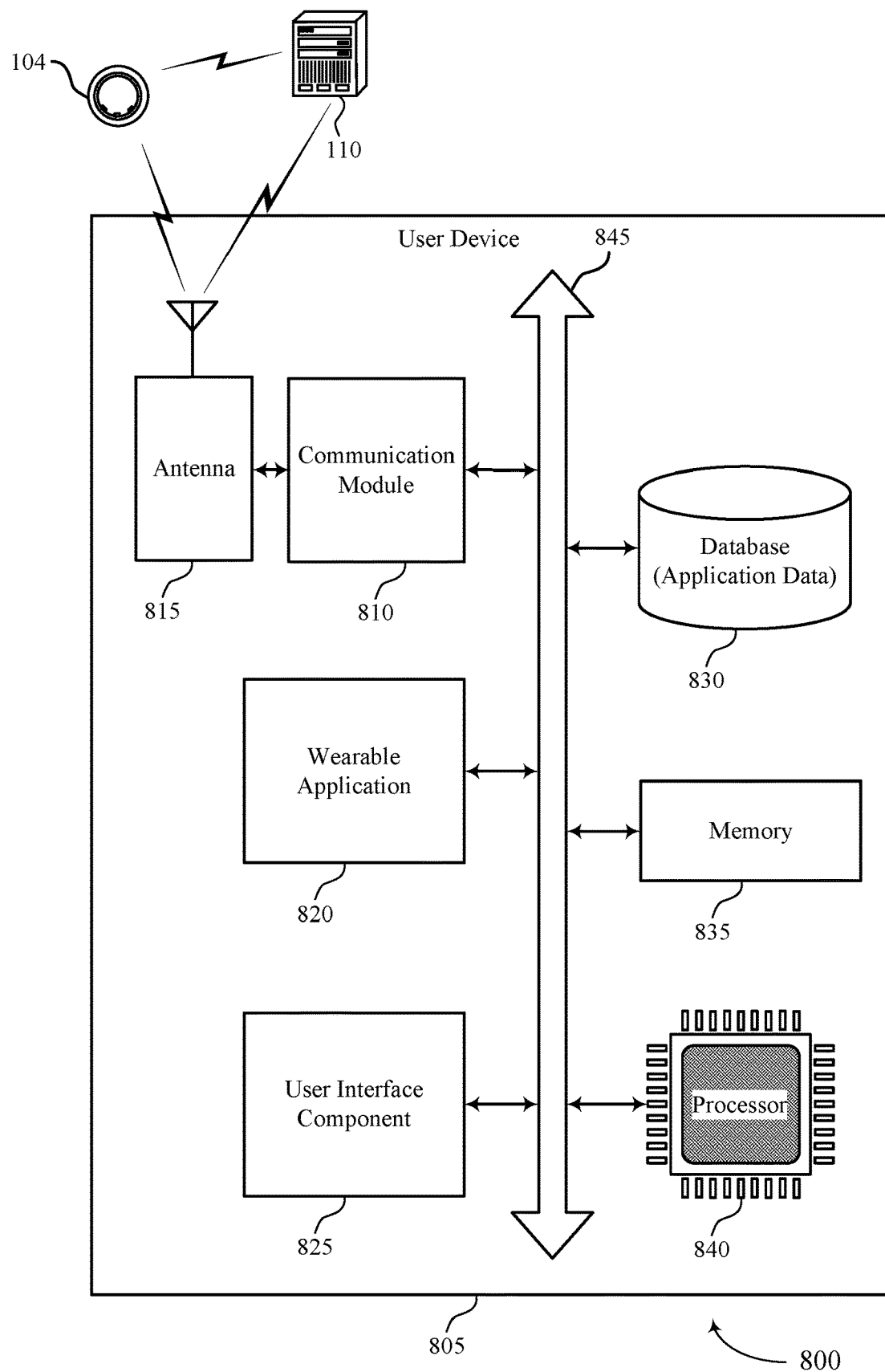
FIG. 8 shows a diagram of a system including a device that supports techniques for gesture recognition using wearable device data in accordance with aspects of the present disclosure.

FIG. 8 shows a diagram of a system 800 including a device 805 that supports techniques for gesture recognition using wearable device data in accordance with aspects of the present disclosure. The device 805 may be an example of or include the components of a device 605 as described herein. The device 805 may include an example of a user device 106, as described previously herein. The device 805 may include components for bi-directional communications including components for transmitting and receiving communications with a wearable device 104 and a server 110, such as a wearable application 820, a communication module 810, an antenna 815, a user interface component 825, a database (application data) 830, a memory 835, and a processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-b of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, which may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a BIOS which may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

For example, the wearable application 820 may be configured as or otherwise support a means for receiving geographical location data associated with a user throughout a time interval. The wearable application 820 may be configured as or otherwise support a means for identifying a set of gesture profiles corresponding to a set of gestures associated with the geographical location data of the user, wherein the set of gestures are included within a plurality of gestures defined within an application associated with a wearable device. The wearable application 820 may be configured as or otherwise support a means for acquiring physiological data associated with the user from the wearable device, the physiological data comprising at least motion data. The wearable application 820 may be configured as or otherwise support a means for identifying a plurality of motion segments within the time interval based at least in part on the motion data. The wearable application 820 may be configured as or otherwise support a means for identifying a gesture the user engaged in based at least in part on matching a motion segment of the plurality of motion segments to a gesture profile of the set of gesture profiles. The wearable application 820 may be configured as or otherwise support a means for causing a GUI of a user device running the application to display an indication of the gesture.

By including or configuring the wearable application 820 in accordance with examples as described herein, the device 805 may support techniques for gesture recognition using wearable device data which may result in increased gesture recognition accuracy, reduced latency of gesture recognition, improved user experience related to reduced processing, reduced power consumption, improved coordination between devices, longer battery life, and improved utilization of processing capability, among other advantages.

The wearable application 820 may include an application (e.g., "app"), program, software, or other component that is configured to facilitate communications with a ring 104, server 110, other user devices 106, and the like. For example, the wearable application 820 may include an application executable on a user device 106 that is configured to receive data (e.g., physiological data) from a ring 104, perform processing operations on the received data, transmit and receive data with the servers 110, and cause presentation of data to a user 102.

Figure 9:
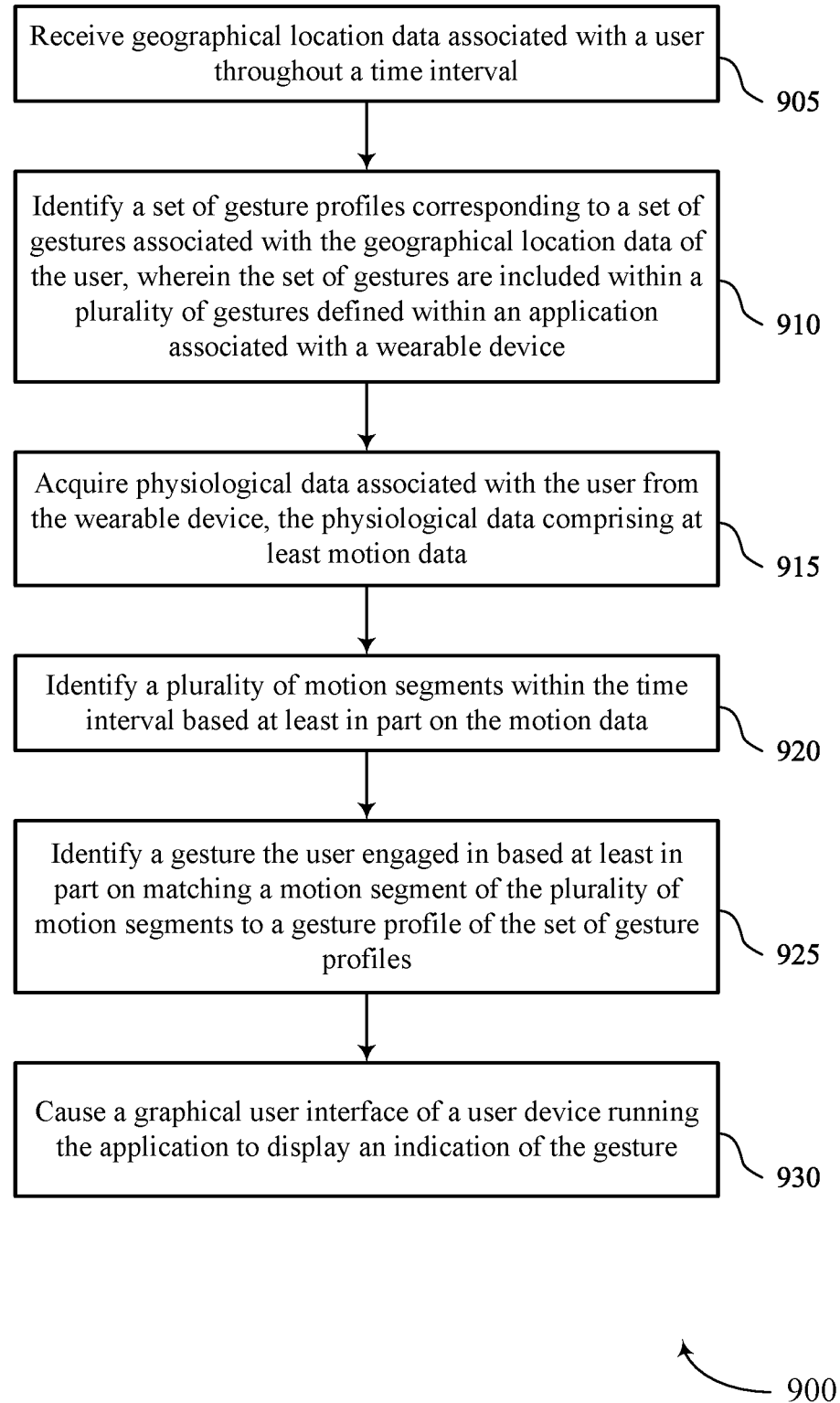
FIGS. 9-12 show flowcharts that support techniques for gesture recognition using wearable device data in accordance with aspects of the present disclosure.

FIG. 9 shows a flowchart illustrating a method 900 that supports techniques for gesture recognition using a wearable device and location data in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 905, the method may include receiving geographical location data associated with a user throughout a time interval. The operations of 905 may be performed in accordance with examples as disclosed herein. In some examples, aspects of the operations of 905 may be performed by a location manager 725 as described with reference to FIG. 7.

At 910, the method may include identifying a set of gesture profiles corresponding to a set of gestures associated with the geographical location data of the user, wherein the set of gestures are included within a plurality of gestures defined within an application associated with a wearable device. The operations of 910 may be performed in accordance with examples as disclosed herein. In some examples, aspects of the operations of 910 may be performed by a gesture profile manager 730 as described with reference to FIG. 7.

At 915, the method may include acquiring physiological data associated with the user from the wearable device, the physiological data comprising at least motion data. The operations of 915 may be performed in accordance with examples as disclosed herein. In some examples, aspects of the operations of 915 may be performed by a data acquisition manager 735 as described with reference to FIG. 7.

At 920, the method may include identifying a plurality of motion segments within the time interval based at least in part on the motion data. The operations of 920 may be performed in accordance with examples as disclosed herein. In some examples, aspects of the operations of 920 may be performed by a data acquisition manager 735 as described with reference to FIG. 7.

At 925, the method may include identifying a gesture the user engaged in based at least in part on matching a motion segment of the plurality of motion segments to a gesture profile of the set of gesture profiles. The operations of 925 may be performed in accordance with examples as disclosed herein. In some examples, aspects of the operations of 925 may be performed by a gesture profile manager 730 as described with reference to FIG. 7.

At 930, the method may include causing a GUI of a user device running the application to display an indication of the gesture. The operations of 930 may be performed in accordance with examples as disclosed herein. In some examples, aspects of the operations of 930 may be performed by a user interface manager 740 as described with reference to FIG. 7.

Figure 10:
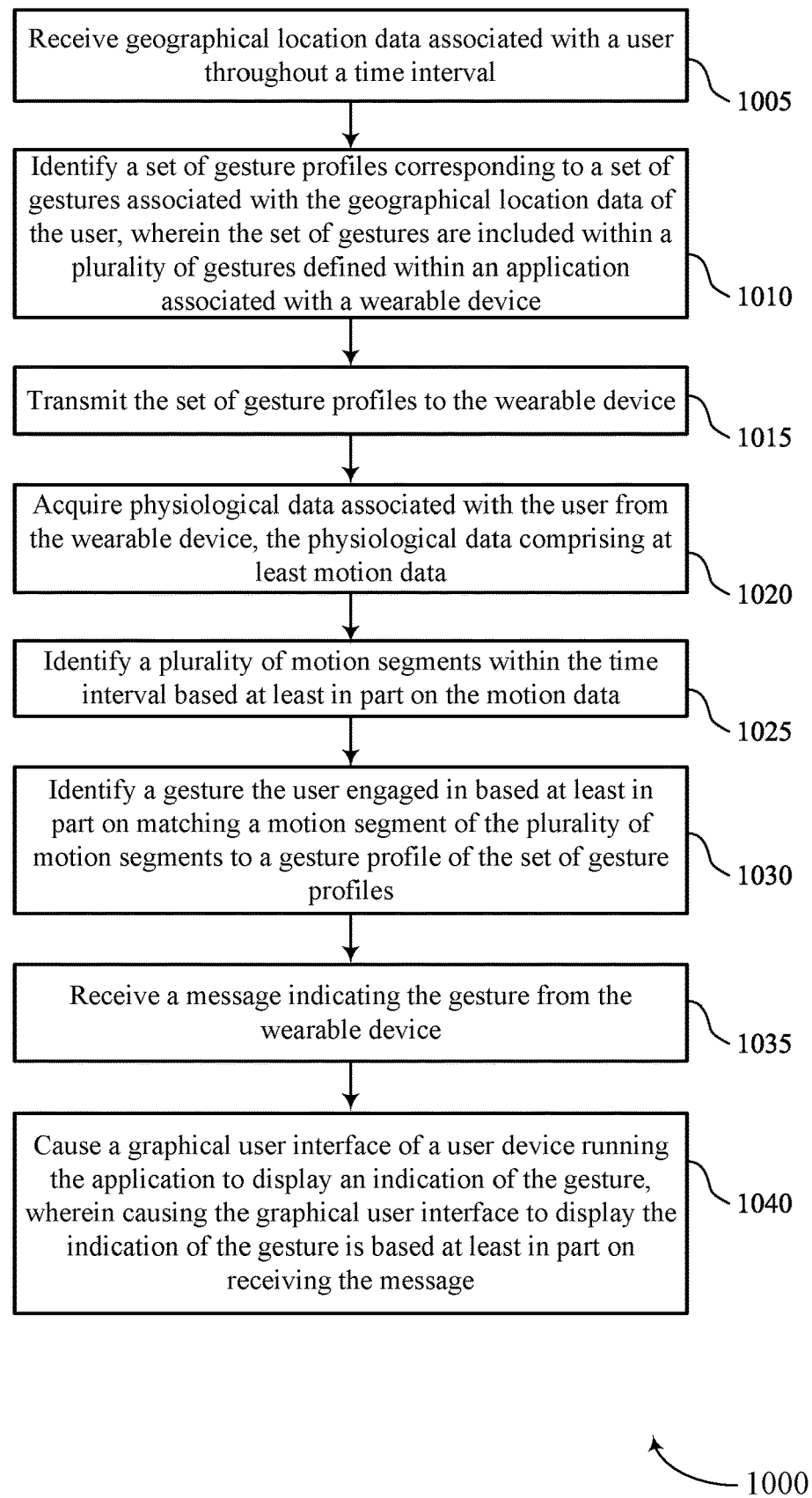

FIG. 10 shows a flowchart illustrating a method 1000 that supports techniques for gesture recognition using a wearable device and location data in accordance with aspects of the present disclosure. The operations of the method 1000 may be implemented by a user device or its components as described herein. For example, the operations of the method 1000 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1005, the method may include receiving geographical location data associated with a user throughout a time interval. The operations of 1005 may be performed in accordance with examples as disclosed herein. In some examples, aspects of the operations of 1005 may be performed by a location manager 725 as described with reference to FIG. 7.

At 1010, the method may include identifying a set of gesture profiles corresponding to a set of gestures associated with the geographical location data of the user, wherein the set of gestures are included within a plurality of gestures defined within an application associated with a wearable device. The operations of 1010 may be performed in accordance with examples as disclosed herein. In some examples, aspects of the operations of 1010 may be performed by a gesture profile manager 730 as described with reference to FIG. 7.

At 1015, the method may include transmitting the set of gesture profiles to the wearable device. The operations of 1015 may be performed in accordance with examples as disclosed herein. In some examples, aspects of the operations of 1015 may be performed by a gesture profile manager 730 as described with reference to FIG. 7.

At 1020, the method may include acquiring physiological data associated with the user from the wearable device, the physiological data comprising at least motion data. The operations of 1020 may be performed in accordance with examples as disclosed herein. In some examples, aspects of the operations of 1020 may be performed by a data acquisition manager 735 as described with reference to FIG. 7.

At 1025, the method may include identifying a plurality of motion segments within the time interval based at least in part on the motion data. The operations of 1025 may be performed in accordance with examples as disclosed herein. In some examples, aspects of the operations of 1025 may be performed by a data acquisition manager 735 as described with reference to FIG. 7.

At 1030, the method may include identifying a gesture the user engaged in based at least in part on matching a motion segment of the plurality of motion segments to a gesture profile of the set of gesture profiles. The operations of 1030 may be performed in accordance with examples as disclosed herein. In some examples, aspects of the operations of 1030 may be performed by a gesture profile manager 730 as described with reference to FIG. 7.

At 1035, the method may include receiving a message indicating the gesture from the wearable device. The operations of 1035 may be performed in accordance with examples as disclosed herein. In some examples, aspects of the operations of 1035 may be performed by a gesture profile manager 730 as described with reference to FIG. 7.

At 1040, the method may include causing a GUI of a user device running the application to display an indication of the gesture, wherein causing the GUI to display the indication of the gesture is based at least in part on receiving the message. The operations of 1040 may be performed in accordance with examples as disclosed herein. In some examples, aspects of the operations of 1040 may be performed by a user interface manager 740 as described with reference to FIG. 7.

Figure 11:
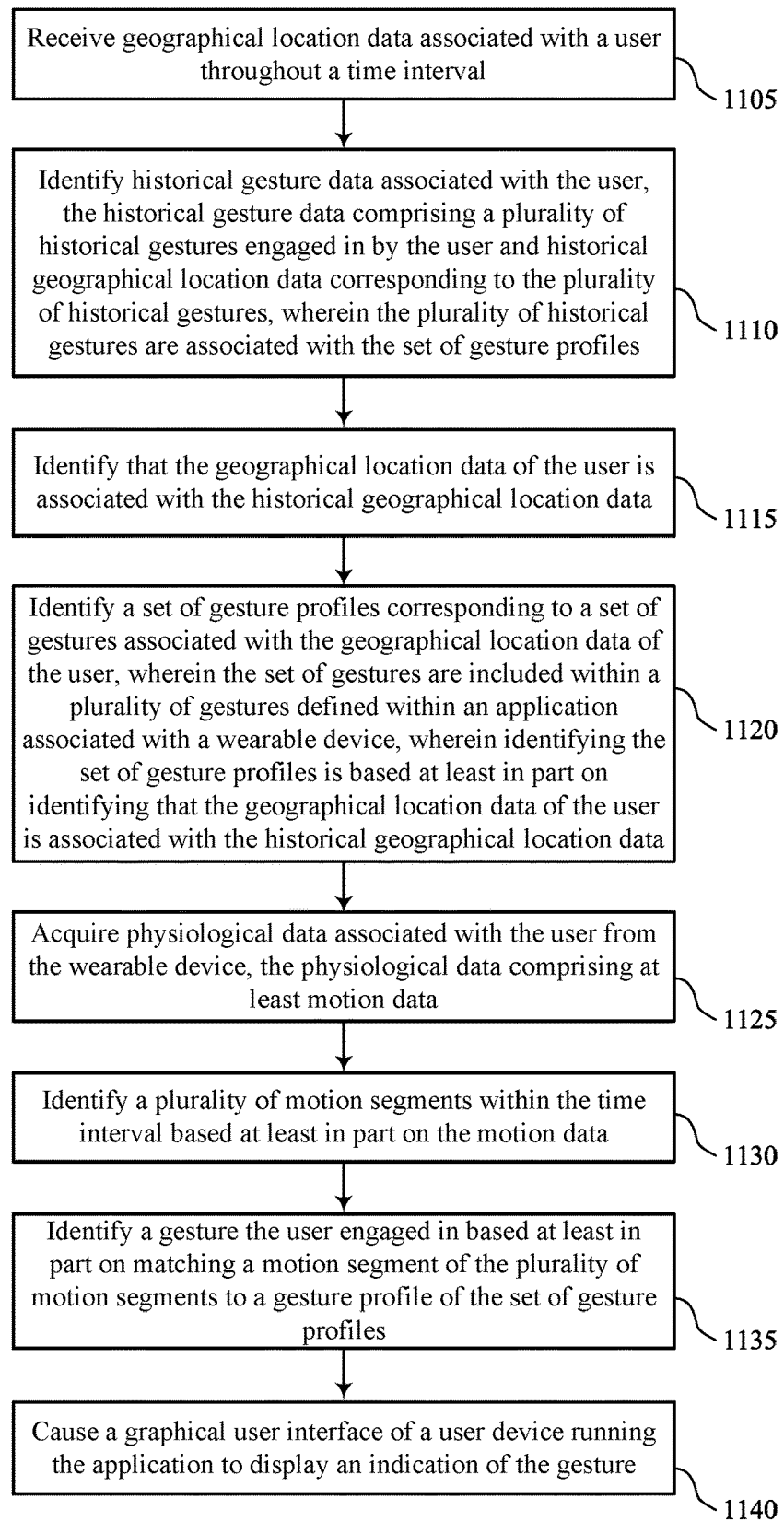

FIG. 11 shows a flowchart illustrating a method 1100 that supports techniques for gesture recognition using a wearable device and location data in accordance with aspects of the present disclosure. The operations of the method 1100 may be implemented by a user device or its components as described herein. For example, the operations of the method 1100 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1105, the method may include receiving geographical location data associated with a user throughout a time interval. The operations of 1105 may be performed in accordance with examples as disclosed herein. In some examples, aspects of the operations of 1105 may be performed by a location manager 725 as described with reference to FIG. 7.

At 1110, the method may include identifying historical gesture data associated with the user, the historical gesture data comprising a plurality of historical gestures engaged in by the user and historical geographical location data corresponding to the plurality of historical gestures, wherein the plurality of historical gestures are associated with the set of gesture profiles. The operations of 1110 may be performed in accordance with examples as disclosed herein. In some examples, aspects of the operations of 1110 may be performed by a gesture profile manager 730 as described with reference to FIG. 7.

At 1115, the method may include identifying that the geographical location data of the user is associated with the historical geographical location data. The operations of 1115 may be performed in accordance with examples as disclosed herein. In some examples, aspects of the operations of 1115 may be performed by a location manager 725 as described with reference to FIG. 7.

At 1120, the method may include identifying a set of gesture profiles corresponding to a set of gestures associated with the geographical location data of the user, wherein the set of gestures are included within a plurality of gestures defined within an application associated with a wearable device, wherein identifying the set of gesture profiles is based at least in part on identifying that the geographical location data of the user is associated with the historical geographical location data. The operations of 1120 may be performed in accordance with examples as disclosed herein. In some examples, aspects of the operations of 1120 may be performed by a gesture profile manager 730 as described with reference to FIG. 7.

At 1125, the method may include acquiring physiological data associated with the user from the wearable device, the physiological data comprising at least motion data. The operations of 1125 may be performed in accordance with examples as disclosed herein. In some examples, aspects of the operations of 1125 may be performed by a data acquisition manager 735 as described with reference to FIG. 7.

At 1130, the method may include identifying a plurality of motion segments within the time interval based at least in part on the motion data. The operations of 1130 may be performed in accordance with examples as disclosed herein. In some examples, aspects of the operations of 1130 may be performed by a data acquisition manager 735 as described with reference to FIG. 7.

At 1135, the method may include identifying a gesture the user engaged in based at least in part on matching a motion segment of the plurality of motion segments to a gesture profile of the set of gesture profiles. The operations of 1135 may be performed in accordance with examples as disclosed herein. In some examples, aspects of the operations of 1135 may be performed by a gesture profile manager 730 as described with reference to FIG. 7.

At 1140, the method may include causing a GUI of a user device running the application to display an indication of the gesture. The operations of 1140 may be performed in accordance with examples as disclosed herein. In some examples, aspects of the operations of 1140 may be performed by a user interface manager 740 as described with reference to FIG. 7.

Figure 12:
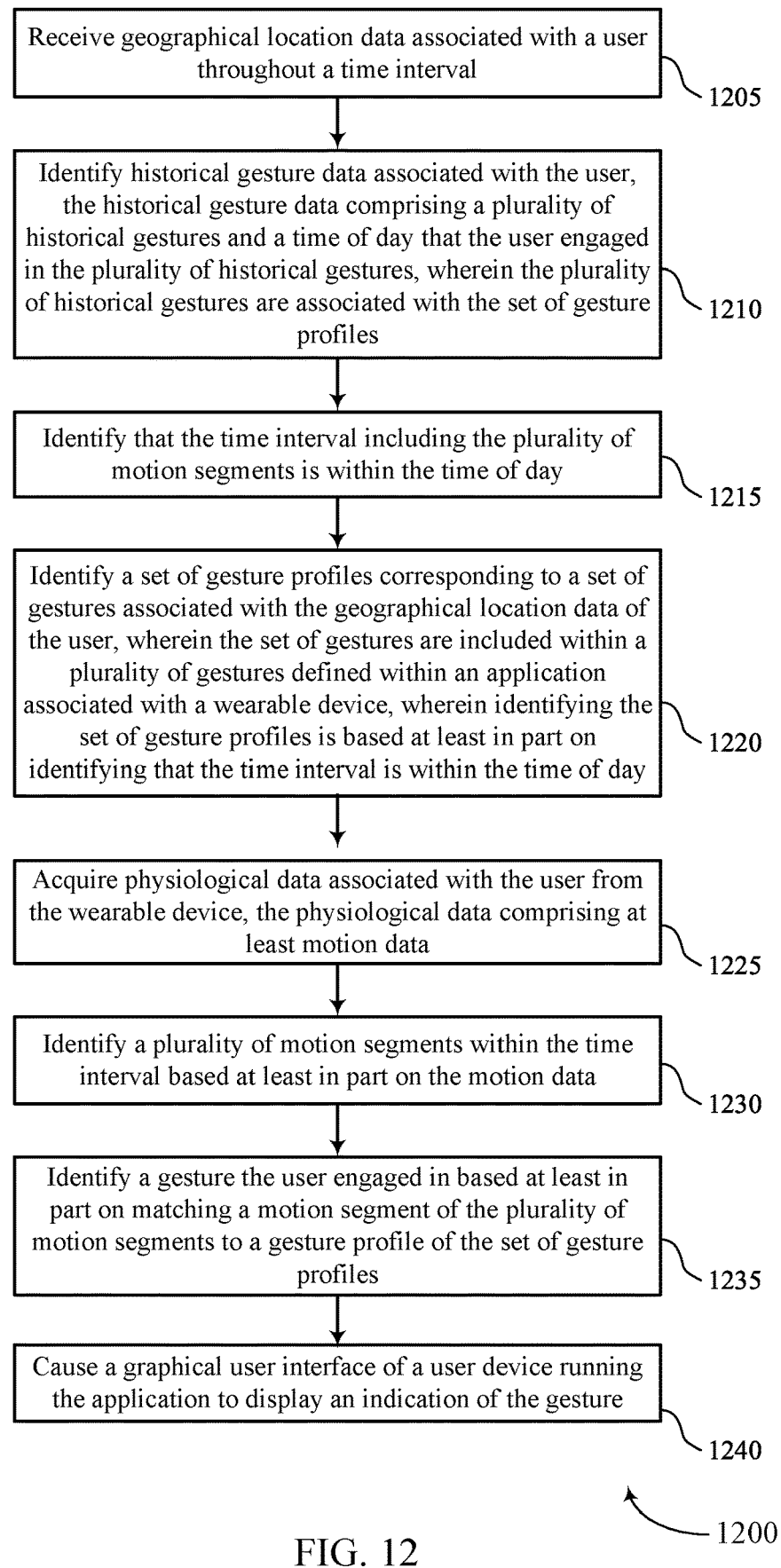

FIG. 12 shows a flowchart illustrating a method 1200 that supports techniques for gesture recognition using a wearable device and location data in accordance with aspects of the present disclosure. The operations of the method 1200 may be implemented by a user device or its components as described herein. For example, the operations of the method 1200 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1205, the method may include receiving geographical location data associated with a user throughout a time interval. The operations of 1205 may be performed in accordance with examples as disclosed herein. In some examples, aspects of the operations of 1205 may be performed by a location manager 725 as described with reference to FIG. 7.

At 1210, the method may include identifying historical gesture data associated with the user, the historical gesture data comprising a plurality of historical gestures and a time of day that the user engaged in the plurality of historical gestures, wherein the plurality of historical gestures are associated with the set of gesture profiles. The operations of 1210 may be performed in accordance with examples as disclosed herein. In some examples, aspects of the operations of 1210 may be performed by a gesture profile manager 730 as described with reference to FIG. 7.

At 1215, the method may include identifying that the time interval including the plurality of motion segments is within the time of day. The operations of 1215 may be performed in accordance with examples as disclosed herein. In some examples, aspects of the operations of 1215 may be performed by a time manager 745 as described with reference to FIG. 7.

At 1220, the method may include identifying a set of gesture profiles corresponding to a set of gestures associated with the geographical location data of the user, wherein the set of gestures are included within a plurality of gestures defined within an application associated with a wearable device, wherein identifying the set of gesture profiles is based at least in part on identifying that the time interval is within the time of day. The operations of 1220 may be performed in accordance with examples as disclosed herein. In some examples, aspects of the operations of 1220 may be performed by a gesture profile manager 730 as described with reference to FIG. 7.

At 1225, the method may include acquiring physiological data associated with the user from the wearable device, the physiological data comprising at least motion data. The operations of 1225 may be performed in accordance with examples as disclosed herein. In some examples, aspects of the operations of 1225 may be performed by a data acquisition manager 735 as described with reference to FIG. 7.

At 1230, the method may include identifying a plurality of motion segments within the time interval based at least in part on the motion data. The operations of 1230 may be performed in accordance with examples as disclosed herein. In some examples, aspects of the operations of 1230 may be performed by a data acquisition manager 735 as described with reference to FIG. 7.

At 1235, the method may include identifying a gesture the user engaged in based at least in part on matching a motion segment of the plurality of motion segments to a gesture profile of the set of gesture profiles. The operations of 1235 may be performed in accordance with examples as disclosed herein. In some examples, aspects of the operations of 1235 may be performed by a gesture profile manager 730 as described with reference to FIG. 7.

At 1240, the method may include causing a GUI of a user device running the application to display an indication of the gesture. The operations of 1240 may be performed in accordance with examples as disclosed herein. In some examples, aspects of the operations of 1240 may be performed by a user interface manager 740 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method is described. The method may include receiving geographical location data associated with a user throughout a time interval, identifying a set of gesture profiles corresponding to a set of gestures associated with the geographical location data of the user, wherein the set of gestures are included within a plurality of gestures defined within an application associated with a wearable device, acquiring physiological data associated with the user from the wearable device, the physiological data comprising at least motion data, identifying a plurality of motion segments within the time interval based at least in part on the motion data, identifying a gesture the user engaged in based at least in part on matching a motion segment of the plurality of motion segments to a gesture profile of the set of gesture profiles, and causing a GUI of a user device running the application to display an indication of the gesture.

An apparatus is described. The apparatus may include a processor, memory coupled with the processor, and instructions stored in the memory. The instructions may be executable by the processor to cause the apparatus to receive geographical location data associated with a user throughout a time interval, identify a set of gesture profiles corresponding to a set of gestures associated with the geographical location data of the user, wherein the set of gestures are included within a plurality of gestures defined within an application associated with a wearable device, acquire physiological data associated with the user from the wearable device, the physiological data comprising at least motion data, identify a plurality of motion segments within the time interval based at least in part on the motion data, identify a gesture the user engaged in based at least in part on matching a motion segment of the plurality of motion segments to a gesture profile of the set of gesture profiles, and cause a GUI of a user device running the application to display an indication of the gesture.

Another apparatus is described. The apparatus may include means for receiving geographical location data associated with a user throughout a time interval, means for identifying a set of gesture profiles corresponding to a set of gestures associated with the geographical location data of the user, wherein the set of gestures are included within a plurality of gestures defined within an application associated with a wearable device, means for acquiring physiological data associated with the user from the wearable device, the physiological data comprising at least motion data, means for identifying a plurality of motion segments within the time interval based at least in part on the motion data, means for identifying a gesture the user engaged in based at least in part on matching a motion segment of the plurality of motion segments to a gesture profile of the set of gesture profiles, and means for causing a GUI of a user device running the application to display an indication of the gesture.

A non-transitory computer-readable medium storing code is described. The code may include instructions executable by a processor to receive geographical location data associated with a user throughout a time interval, identify a set of gesture profiles corresponding to a set of gestures associated with the geographical location data of the user, wherein the set of gestures are included within a plurality of gestures defined within an application associated with a wearable device, acquire physiological data associated with the user from the wearable device, the physiological data comprising at least motion data, identify a plurality of motion segments within the time interval based at least in part on the motion data, identify a gesture the user engaged in based at least in part on matching a motion segment of the plurality of motion segments to a gesture profile of the set of gesture profiles, and cause a GUI of a user device running the application to display an indication of the gesture.

Some examples of the method, apparatuses, and non-transitory computer-readable medium described herein may further include operations, features, means, or instructions for transmitting the set of gesture profiles to the wearable device, wherein the wearable device may be configured to identify the gesture by matching the motion segment to the gesture profile from the set of gesture profiles and receiving a message indicating the gesture from the wearable device, wherein causing the GUI to display the indication of the gesture may be based at least in part on receiving the message.

Some examples of the method, apparatuses, and non-transitory computer-readable medium described herein may further include operations, features, means, or instructions for identifying historical gesture data associated with the user, the historical gesture data comprising a plurality of historical gestures engaged in by the user and historical geographical location data corresponding to the plurality of historical gestures, wherein the plurality of historical gestures may be associated with the set of gesture profiles and identifying that the geographical location data of the user may be associated with the historical geographical location data, wherein identifying the set of gesture profiles may be based at least in part on identifying that the geographical location data of the user may be associated with the historical geographical location data.

Some examples of the method, apparatuses, and non-transitory computer-readable medium described herein may further include operations, features, means, or instructions for identifying historical gesture data associated with the user, the historical gesture data comprising a plurality of historical gestures and a time of day that the user engaged in the plurality of historical gestures, wherein the plurality of historical gestures may be associated with the set of gesture profiles and identifying that the time interval including the plurality of motion segments may be within the time of day, wherein identifying the set of gesture profiles may be based at least in part on identifying that the time interval may be within the time of day.

Some examples of the method, apparatuses, and non-transitory computer-readable medium described herein may further include operations, features, means, or instructions for receiving, via the GUI and based at least in part on displaying the indication of the gesture, a confirmation of the gesture, a modification of the gesture, or both.

Some examples of the method, apparatuses, and non-transitory computer-readable medium described herein may further include operations, features, means, or instructions for identifying, based at least in part on the identified gesture, an activity segment that the user is or was engaged, a taggable event included within a plurality of taggable events defined in the application, or both and causing the GUI of the user device to display an indication of the activity segment, an indication of the taggable event, or both.

Some examples of the method, apparatuses, and non-transitory computer-readable medium described herein may further include operations, features, means, or instructions for receiving, via the GUI, a user input indicating a semantic location and the set of gestures associated with the semantic location and identifying that the geographical location data may be associated with the semantic location, wherein identifying the set of gesture profiles may be based at least in part on identifying the geographical location data may be associated with the semantic location.

Some examples of the method, apparatuses, and non-transitory computer-readable medium described herein may further include operations, features, means, or instructions for receiving additional physiological data associated with the user from the wearable device, the additional physiological data comprising additional motion data including an additional motion segment, receiving, via the GUI, a user input indicating that the additional motion segment may be associated with the gesture, and generating the gesture profile associated with the gesture based at least in part on the user input, wherein identifying the gesture may be based at least in part on generating the gesture profile.

Some examples of the method, apparatuses, and non-transitory computer-readable medium described herein may further include operations, features, means, or instructions for identifying a relationship between the identified gesture and the physiological data acquired during the time interval, additional physiological data acquired during a different time interval, or both and causing the GUI of the user device to display a message associated with the relationship.

In some examples of the method, apparatuses, and non-transitory computer-readable medium described herein, selectively adjusting a Readiness Score associated with the user, an Activity Score associated with the user, or both, based at least in part on the identified gesture.

In some examples of the method, apparatuses, and non-transitory computer-readable medium described herein, the geographical location data comprises geographical positioning data acquired via the user device.

In some examples of the method, apparatuses, and non-transitory computer-readable medium described herein, the geographical location data may be received via a calendar application executable by the user device.

In some examples of the method, apparatuses, and non-transitory computer-readable medium described herein, the set of gestures comprise an eating gesture, a drinking gesture, a sports-related gesture, or any combination thereof.

In some examples of the method, apparatuses, and non-transitory computer-readable medium described herein, the sports-related gesture comprises a swimming stroke gesture, a racket sport gesture, a walking or running stride gesture, a golf swing gesture, a weight-lifting gesture, or the like thereof.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow, capillary blood flow, arteriole blood flow, or a combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for gesture recognition, comprising:
  receiving geographical location data associated with a user throughout a time interval;
  identifying a set of gesture profiles corresponding to a set of gestures associated with the geographical location data of the user, wherein the set of gestures are a subset of a plurality of gestures defined within an application associated with a wearable device, and wherein each gesture profile of the set of gesture profiles corresponds to one or more motion segments of a respective gesture from the set of gestures;
  acquiring physiological data associated with the user from the wearable device, the physiological data comprising at least motion data;
  identifying a plurality of motion segments within the time interval based at least in part on the motion data;
  identifying a gesture the user engaged in based at least in part on matching a motion segment of the plurality of motion segments to a gesture profile of the set of gesture profiles; and
  causing a graphical user interface of a user device running the application to display an indication of the gesture performed by the user.

2. The method of claim 1, further comprising:
  transmitting the set of gesture profiles to the wearable device, wherein the wearable device is configured to identify the gesture by matching the motion segment to the gesture profile from the set of gesture profiles; and
  receiving a message indicating the gesture from the wearable device, wherein causing the graphical user interface to display the indication of the gesture is based at least in part on receiving the message.

3. The method of claim 1, further comprising:
  identifying historical gesture data associated with the user, the historical gesture data comprising a plurality of historical gestures engaged in by the user and historical geographical location data corresponding to the plurality of historical gestures, wherein the plurality of historical gestures are associated with the set of gesture profiles; and
  identifying that the geographical location data of the user is associated with the historical geographical location data, wherein identifying the set of gesture profiles is based at least in part on identifying that the geographical location data of the user is associated with the historical geographical location data.

4. The method of claim 1, further comprising:
  identifying historical gesture data associated with the user, the historical gesture data comprising a plurality of historical gestures and a time of day that the user engaged in the plurality of historical gestures, wherein the plurality of historical gestures are associated with the set of gesture profiles; and
  identifying that the time interval including the plurality of motion segments is within the time of day, wherein identifying the set of gesture profiles is based at least in part on identifying that the time interval is within the time of day.

5. The method of claim 1, further comprising:
  receiving, via the graphical user interface and based at least in part on displaying the indication of the gesture, a confirmation of the gesture, a modification of the gesture, or both.

6. The method of claim 1, further comprising:
  identifying, based at least in part on the identified gesture, an activity segment that the user is or was engaged, a taggable event included within a plurality of taggable events defined in the application, or both; and
  causing the graphical user interface of the user device to display an indication of the activity segment, an indication of the taggable event, or both.

7. The method of claim 1, further comprising:
  receiving, via the graphical user interface, a user input indicating a semantic location and the set of gestures associated with the semantic location; and
  identifying that the geographical location data is associated with the semantic location, wherein identifying the set of gesture profiles is based at least in part on identifying the geographical location data is associated with the semantic location.

8. The method of claim 1, further comprising:
  receiving additional physiological data associated with the user from the wearable device, the additional physiological data comprising additional motion data including an additional motion segment;
  receiving, via the graphical user interface, a user input indicating that the additional motion segment is associated with the gesture; and
  generating the gesture profile associated with the gesture based at least in part on the user input, wherein identifying the gesture is based at least in part on generating the gesture profile.

9. The method of claim 1, further comprising:
  identifying a relationship between the identified gesture and the physiological data acquired during the time interval, additional physiological data acquired during a different time interval, or both; and causing the graphical user interface of the user device to display a message associated with the relationship.

10. The method of claim 1, further comprising:
selectively adjusting a Readiness Score associated with the user, an Activity Score associated with the user, or both, based at least in part on the identified gesture.

11. The method of claim 1, wherein the geographical location data comprises geographical positioning data acquired via the user device.

12. The method of claim 1, wherein the geographical location data is received via a calendar application executable by the user device.

13. The method of claim 1, wherein the set of gestures comprise an eating gesture, a drinking gesture, a sports-related gesture, or any combination thereof.

14. The method of claim 13, wherein the sports-related gesture comprises a swimming stroke gesture, a racket sport gesture, a walking or running stride gesture, a golf swing gesture, a weight-lifting gesture, or any combination thereof.

15. The method of claim 1, wherein the wearable device comprises a wearable ring device.

16. The method of claim 1, wherein the wearable device collects the physiological data from the user based on arterial blood flow, capillary blood flow, arteriole blood flow, or a combination thereof.

17. An apparatus, comprising:
a processor;
memory coupled with the processor; and
instructions stored in the memory and executable by the processor to cause the apparatus to:
receive geographical location data associated with a user throughout a time interval;
identify a set of gesture profiles corresponding to a set of gestures associated with the geographical location data of the user, wherein the set of gestures are a subset of a plurality of gestures defined within an application associated with a wearable device, and wherein each gesture profile of the set of gesture profiles corresponds to one or more motion segments of a respective gesture from the set of gestures;
acquire physiological data associated with the user from the wearable device, the physiological data comprising at least motion data;
identify a plurality of motion segments within the time interval based at least in part on the motion data;
identify a gesture the user engaged in based at least in part on matching a motion segment of the plurality of motion segments to a gesture profile of the set of gesture profiles; and
cause a graphical user interface of a user device running the application to display an indication of the gesture performed by the user.

18. The apparatus of claim 17, wherein the instructions are further executable by the processor to cause the apparatus to:
transmit the set of gesture profiles to the wearable device, wherein the wearable device is configured to identify the gesture by matching the motion segment to the gesture profile from the set of gesture profiles; and
receive a message indicating the gesture from the wearable device, wherein causing the graphical user interface to display the indication of the gesture is based at least in part on receiving the message.

19. The apparatus of claim 17, wherein the instructions are further executable by the processor to cause the apparatus to:
identify historical gesture data associated with the user, the historical gesture data comprising a plurality of historical gestures engaged in by the user and historical geographical location data corresponding to the plurality of historical gestures, wherein the plurality of historical gestures are associated with the set of gesture profiles; and
identify that the geographical location data of the user is associated with the historical geographical location data, wherein identifying the set of gesture profiles is based at least in part on identifying that the geographical location data of the user is associated with the historical geographical location data.

20. A non-transitory computer-readable medium storing code, the code comprising instructions executable by a processor to:
receive geographical location data associated with a user throughout a time interval;
identify a set of gesture profiles corresponding to a set of gestures associated with the geographical location data of the user, wherein the set of gestures are a subset of a plurality of gestures defined within an application associated with a wearable device, and wherein each gesture profile of the set of gesture profiles corresponds to a respective motion segment of a respective gesture from the set of gestures;
acquire physiological data associated with the user from the wearable device, the physiological data comprising at least motion data;
identify a plurality of motion segments within the time interval based at least in part on the motion data;
identify a gesture the user engaged in based at least in part on matching a motion segment of the plurality of motion segments to a gesture profile of the set of gesture profiles; and
cause a graphical user interface of a user device running the application to display an indication of the gesture performed by the user.

* * * * *